United States Patent
Shin et al.

(10) Patent No.: US 9,457,055 B2
(45) Date of Patent: Oct. 4, 2016

(54) **METHOD FOR TREATING INFLAMMATION, ARTHRITIS OR DISC DISEASES USING A MIXED EXTRACT OF CIBOTII RHIZOMA, LEDEBOURIELLAE RADIX, ACHYRANTHIS RADIX, *PAEONIA LACTIFLORA* PALL AND GLYCYRRHIZAE RADIX**

(71) Applicant: Joon-Sik Shin, Seoul (KR)

(72) Inventors: Joon-Sik Shin, Seoul (KR); Jin Ho Lee, Seoul (KR)

(73) Assignee: Joon-Sik Shin (KR)

( * ) Notice: Subject to any disclaimer, the term of this patent is extended or adjusted under 35 U.S.C. 154(b) by 197 days.

(21) Appl. No.: 14/273,810

(22) Filed: May 9, 2014

(65) Prior Publication Data

US 2015/0320819 A1 Nov. 12, 2015

(51) Int. Cl.

| | |
|---|---|
| *A61K 36/48* | (2006.01) |
| *A61K 36/65* | (2006.01) |
| *A61K 36/185* | (2006.01) |
| *A61K 36/12* | (2006.01) |
| *A61K 36/23* | (2006.01) |
| *A61K 36/484* | (2006.01) |
| *A61K 36/21* | (2006.01) |
| *A61K 36/11* | (2006.01) |
| *A61K 36/238* | (2006.01) |

(52) U.S. Cl.
CPC ............... *A61K 36/65* (2013.01); *A61K 36/11* (2013.01); *A61K 36/12* (2013.01); *A61K 36/21* (2013.01); *A61K 36/23* (2013.01); *A61K 36/238* (2013.01); *A61K 36/484* (2013.01); *A61K 2236/00* (2013.01)

(58) Field of Classification Search
None
See application file for complete search history.

(56) References Cited

FOREIGN PATENT DOCUMENTS

| CN | 1931320 A | * | 3/2007 |
|---|---|---|---|
| CN | 101121017 A | * | 2/2008 |
| CN | 102743492 A | * | 10/2012 |

OTHER PUBLICATIONS

Bang et al., "Achyranthes japonica exhibits anti-inflammatory effect via NF-kB suppression and HO-1 induction in macrophages," Journal of Ethnopharmacology, 2012, vol. 144, pp. 109-117.

Cho et al., "Hexane/ethanol extract of Glycyrrhiza uralensis licorice exerts potent anti-inflammatory effects in murine macrophages and in mouse skin," Food Chemistry, 2010, vol. 121, pp. 959-966.

Choi, "Liquiritigenin isolated from Glycyrrhiza uralensis stimulates osteoblast function in osteoblastic MC3T3-E1 cells," International Immunopharmacology, 2012, vol. 12, pp. 139-143.

Jiang et al., "Influence of Paeonia lactiflora roots extract on cAMP-phosphodiesterase activity and related anti-inflammatory action," Journal of Ethnopharmacology, 2011, vol. 137, pp. 914-920.

Kong et al., "The suppressive effects of Saposhnikovia divaricata (Fangfeng) chromone extract on rheumatoid arthritis via inhibition of nuclear factor-κB and mitogen activated proteinkinases activation on collagen-induced arthritis model," Journal of Enthnopharmacology, 2013, vol. 148, pp. 842-850.

Lee et al., "Anti-inflammatory and anti-osteoarthritis effects of fermented Achyranthes japonica Nakai," Journal of Ethnopharmacology, 2012, vol. 142, pp. 634-641.

Xu et al., "Pharmacokinetic comparisons of two different combinations of Shaoyao-Gancao Decoction in rats: Competing mechanisms between paeoniflorin and glycyrrhetinic acid," Journal of Ethnopharmacology, 2013, vol. 149, pp. 443-452.

Zhang et al., "Mechanisms involved in the therapeutic effects of Paeonia lactiflora Pallas in rheumatoid arthritis," International Immunopharmacology, 2012, vol. 14, pp. 27-31.

Zhao et al., "Anti-osteoporosis activity of Cibotium barometz extract on ovariectomy-induced bone loss in rats," Journal of Ethnopharmacology, 2011, vol. 137, pp. 1083-1088.

\* cited by examiner

*Primary Examiner* — Chris R Tate
*Assistant Examiner* — Randall Winston
(74) *Attorney, Agent, or Firm* — Sheridan Ross P.C.

(57) ABSTRACT

The present invention relates to a method for treating inflammation, arthritis or disc diseases using a pharmaceutically effective amount of a mixed extract of Cibotii Rhizoma, Ledebouriellae Radix, Achyranthis Radix, *Paeonia lactiflora* Pall, and Glycyrrhizae Radix according to the present invention, and since the mixed extract of Cibotii Rhizoma, Ledebouriellae Radix, Achyranthis Radix, *Paeonia lactiflora* Pall, and Glycyrrhizae Radix increased the survival rate of macrophages in vitro, decreased the production of NO, which is involved in anti-inflammation, inhibited all of COX-2, iNOS and MMP expressions, showed nerve cell regenerative and protective effects, exhibited pain-inhibitory effect and arthritis edema-inhibitory effects in vivo, and showed disc volume decrease and absorption effect in patients of disc diseases, the mixed extract of Cibotii Rhizoma, Ledebouriellae Radix, Achyranthis Radix, *Paeonia lactiflora* Pall, and Glycyrrhizae Radix could be used effectively for methods for treating inflammation, arthritis, or disc diseases.

12 Claims, 12 Drawing Sheets

METHOD FOR TREATING INFLAMMATION, ARTHRITIS OR DISC DISEASES USING A MIXED EXTRACT OF CIBOTII RHIZOMA, LEDEBOURIELLAE RADIX, ACHYRANTHIS RADIX, *PAEONIA LACTIFLORA* PALL AND GLYCYRRHIZAE RADIX

BACKGROUND OF THE INVENTION

1. Field of the Invention

The present invention relates to a method for treating inflammatory or degenerative diseases by administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

2. Description of the Related Art

Inflammation is a biological defense reaction against infection caused by external sources such as external physical and chemical stimuli, bacteria, fungi, viruses, and all sorts of allergens. The inflammatory response is part of innate immune responses, and as in other animals, the human innate immune responses begin when macrophages recognize patterns which present specifically on the cellular surface of pathogens as non-self and attack the pathogens. During the inflammatory response, blood plasma accumulate around the inflammatory site to dilute toxic products released by bacteria, blood stream increases, and symptoms such as erythema, pain, edema, fever and the like are involved.

These inflammatory responses involve various biochemical phenomena, and in particular, nitric oxide synthase (NOS) and cyclooxygenase (COX) which is related to prostaglandin biosynthesis are known to be important mediators of inflammatory responses. Among them, COX-1 is involved in the production of prostaglandin products (hereinafter referred to as "PG") in the inflammatory site as well as in various normal organs and tissues of the human body, i.e. gastrointestinal tract or kidney and the like. In comparison, COX-2 is known to be an enzyme which functions only at sites of inflammation. It has been known that commercially available nonsteroidal anti-inflammatory drugs (referred to as "NSAIDs") such as diclofenac, aspirin and ibuprofen, inhibit COX-1 and COX-2 at the same time or primarily COX-1, and thus, they inhibit PG not only in tissues with inflammation, when administered for long periods, but also inhibit PG that are essential for function maintenance in other tissues such as liver, gastrointestinal tract, or kidney at the same time, causing numerous adverse effects (Isselbcher et al., Harrison's Principles of Internal Medicine, (13th ed)2, pp 1543-1711).

According to Korea National Health and Nutrition Examination Survey in the years 1998 and 2001, arthritis was a chronic disease being common among adults aged 45 years or older, and the prevalence rate of arthritis increased with age, and in 65 years and over population, it accounted for 356.7 persons per one thousand people in 1998 and 364.2 persons per one thousand people in 2001 (Korea National Health and Nutrition Examination Survey, 2001, Ministry of Health and Welfare, Seoul, Korea, p 51). According to the recent "Senior Statistical Reports, 2010", the ratio of Korean 65 years and over population is 11%, and the prevalence rate of chronic degenerative diseases increases along with the ageing of population structure, and the chronic disease of high annual prevalence rate is arthritis which accounts for 43.1% or more (Senior Statistical Reports, 2010, The Statistics Korea, Daejeon, Korea, p 5). Arthritis refers to joint inflammation, often involves pain, stiffness and edema, and its causes are degenerative changes, abnormality of immune system, infection, wound, disturbances of metabolism, etc., and there are more than one hundred kinds (Garner B C et al., 2011, Using animal models in osteoarthritis biomarker research, J Knee Surg 24: 251-264). Among them, osteoarthritis and rheumatoid arthritis (RA) account for 80% of the entire arthritis, and make up the largest part of burden caused by musculoskeletal diseases. When dividing factors associated with the onset of osteoarthritis into large groups, proteolytic enzymes, cytokines, and nitric oxide (NO) are known to be main factors (Wu W et al., 2010, Therapeutic effect of the saponin fraction from *Clematis chinensis* Osbeck roots on osteoarthritis induced by monosodium iodoacetate through protecting articular cartilage. Phytother Res 24: 538-546; Wesche-Soldato D E et al., 2007, The apoptotic pathway as a therapeutic target in sepsis, Curr Drug Targets 8: 493-500; Herrington C et al., 2008, Molecular and cellular themes in inflammation and immunology, J Pathol 214: 123-125; Campo G M et al., 2009, Glycosaminoglycans modulate inflammation and apoptosis in LPS-treated chondrocytes, J Cell Biochem 160: 83-92). The process of metabolism in cartilage tissues plays a pivotal role in the degeneration of cartilage tissues (Phitak T et al., 2009, The effects of p-hydroxycinnamaldehyde from Alpinia galanga extracts on human chondrocytes, Phytochemistry 7: 237-243), and representatively, matrix metalloproteinases (MMPs) are a proteolytic enzyme that destroys matrix components in bone and cartilage, and are expressed also in a pathological condition such as arthritis, and it has been known that MMPs play a major role in etiology (Janusz M J et al., 2001, Moderation of iodoacetate-induced experimental osteoarthritis in rats by matrix metalloproteinase inhibitors, Osteoarthritis Cartilage 9: 751-760; Okada A et al., 2009, Progress of research in osteoarthritis, Metalloproteinases in osteoarthritis, Clin Calcium 19: 1593-1601). Upon the onset of arthritis, MMPs of which expression increases are MMP-1, MMP-2, MMP-3, MMP-8, MMP-9, MMP-7, and MMP-13, and in particular, it was reported that in cases of MMP-7 and MMP-13, their expression is increased in osteoarthritis (Yoshihara Y et al., 2000, Matrix metalloproteinases and tissue inhibitors of metalloproteinases in synovial fluids from patients with rheumatoid arthritis or osteoarthritis, Ann Rheum Dis 59: 455-461).

Recently, various drugs and treatment methods have been developed and used in the treatment of osteoarthritis, but, the main purpose of treatment is to relieve pain, maintain joint function, and prevent disability caused by dysfunction of joint. Treatment methods of arthritis are being focused on removal of pain by taking a simple analgesic, and when arthritis proceeds further and pain continues, anti-inflammatory analgesic drugs having strong anti-inflammatory effect are used. So far, many drugs having analgesic and anti-inflammatory effects have been developed, and include nonsteroidal anti-inflammatory drugs (NSAIDs) such as diclofenac, aspirin, and ibuprofen. However, NSAIDs which are often used for treatment of arthritis have a problem that causes adverse effects to the digestive system, in particular, to a stomach, and this is because NSAIDs inhibit an stomach inner wall protective enzyme, cyclooxygenase 1 (COX-1), and a pain- and inflammation-causing enzyme, cyclooxygenase 2 (COX-2), at the same time. In addition, long-term use of NSAID can lead to a heartburn or ulcer which eventually causes perforation.

Disc pain diseases are an important disease of modern society, costing many billions of dollars of medical finances, and according to United States' National Health Statistics, it has been reported that more than 2% of the population have disc diseases, and five million people show symptoms of spine sprain (Premer, A., S, et, al., 1999; Andersson, G. B., 1999). Also in the South Korea, spine-related pains cause a huge loss in labor force and excessive health expenditure, leading to economic losses.

As biochemical changes, IL-1 of cytokines and proteolytic enzymes such as stromelysin and metalloproteinase (MMP) are found in degenerative disc or extruded disc, and IL-1 was assumed to promote synthesis of metalloproteinase, nitric oxide, prostaglandin E2, etc. in a normal disc and lead to disc degeneration (Kang, J. D., et, al., 1997). Injured discs or discs having degenerative changes become to lose their dynamic function, cause pains, and unlike skin inflammation, edema occur inside, pressure increases and compresses an inflammatory site and its surroundings. In addition, when inflammation occurs, spinal muscles around the lesion become tensed and compress the inflammatory site and its surroundings. This compression acts as a physical stimulus to the lesion, and causes larger inflammation. Accordingly, there is a need to develop natural products and materials which can have excellent efficacy in inflammation, arthritis and disc diseases in human bodies and of which the safety is guaranteed 100 percent.

Thus, the present inventors have made an effort to develop natural products having effective anti-inflammatory activity for arthritis or disc disease, and as a result, have found the fact that: a mixed extract of Cibotii Rhizoma, Ledebouriellae Radix, Achyranthis Radix, *Paeonia lactiflora* Pall and Glycyrrhizae Radix increased the survival rate of macrophages in vitro, decreased NO production effectively, exhibited significant anti-inflammatory effect by inhibiting COX-2, iNOS and MMP expressions, showed nerve cell regenerative and protective effects, exhibited pain-inhibitory effect in vivo, and inhibited arthritis edema and showed clinical pharmacological effect in patients of disc diseases. Accordingly, the present inventors identified that the mixed extract of Cibotii Rhizoma, Ledebouriellae Radix, Achyranthis Radix, *Paeonia lactiflora* Pall and Glycyrrhizae Radix could be used effectively for a method for treating inflammation, arthritis, or disc diseases, and completed the present invention based on the fact.

SUMMARY OF THE INVENTION

One object of the present invention relates to a method for treating inflammation, arthritis, or disc diseases, comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

Another object of the present invention relates to a treatment method of inhibiting arthritis edema comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

Still another object of the present invention relates to a method for treating disc diseases comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

Even another object of the present invention relates to a method for inhibiting inflammatory pain comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

Yet another object of the present invention relates to anti-inflammation, prevention of arthritis or disc diseases, and a pharmaceutical composition, or a health food for improvement of arthritis or disc diseases, containing a mixed extract of Cibotii Rhizoma, Ledebouriellae Radix, Achyranthis Radix, *Paeonia lactiflora* Pall, and Glycyrrhizae Radix as an active ingredient.

Further another object of the present invention relates to prevention of arthritis edema, and a pharmaceutical composition, or a health food for improvement of arthritis edema, containing a mixed extract of Cibotii Rhizoma, Ledebouriellae Radix, Achyranthis Radix, *Paeonia lactiflora* Pall, and Glycyrrhizae Radix as an active ingredient.

Still further another object of the present invention relates to prevention of disc diseases, and a pharmaceutical composition, or a health food for improvement of disc diseases, containing a mixed extract of Cibotii Rhizoma, Ledebouriellae Radix, Achyranthis Radix, *Paeonia lactiflora* Pall, and Glycyrrhizae Radix as an active ingredient.

Even further another object of the present invention relates to prevention of inflammatory pain, and a pharmaceutical composition, or a health food for improvement of inflammatory pain, containing a mixed extract of Cibotii Rhizoma, Ledebouriellae Radix, Achyranthis Radix, *Paeonia lactiflora* Pall, and Glycyrrhizae Radix as an active ingredient.

In order to achieve the objects, the present invention provides a method for treating inflammation, arthritis, or disc diseases, comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

The present invention also provides a method of inhibiting inflammation comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

Furthermore, the present invention provides a treatment method for inhibiting pain comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

The present invention also provides a treatment method of inhibiting edema comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

Furthermore, the present invention provides a method for regenerating nerve cells comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

The present invention also provides a method for protecting nerve cells comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

Furthermore, the present invention provides a method for inhibiting arthritis edema comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

The present invention also provides a method for treating disc diseases comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

Furthermore, the present invention provides a method for inhibiting inflammatory pain comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

The present invention also provides anti-inflammation, prevention of arthritis or disc diseases, and a pharmaceutical composition, or a health food for improvement of arthritis or disc diseases, containing a mixed extract of Cibotii Rhizoma, Ledebouriellae Radix, Achyranthis Radix, *Paeonia lactiflora* Pall, and Glycyrrhizae Radix as an active ingredient.

Furthermore, the present invention provides prevention of arthritis edema, and a pharmaceutical composition, or a health food for improvement of arthritis edema, containing a mixed extract of Cibotii Rhizoma, Ledebouriellae Radix, Achyranthis Radix, *Paeonia lactiflora* Pall, and Glycyrrhizae Radix as an active ingredient.

The present invention also provides prevention of disc diseases, and a pharmaceutical composition, or a health food for improvement of disc diseases, containing a mixed extract of Cibotii Rhizoma, Ledebouriellae Radix, Achyranthis Radix, *Paeonia lactiflora* Pall, and Glycyrrhizae Radix as an active ingredient.

Furthermore, the present invention provides prevention of inflammatory pain, and a pharmaceutical composition, or a health food for improvement of inflammatory pain, containing a mixed extract of Cibotii Rhizoma, Ledebouriellae Radix, Achyranthis Radix, *Paeonia lactiflora* Pall, and Glycyrrhizae Radix as an active ingredient.

The present invention relates to a method for treating inflammation, arthritis or disc diseases using a pharmaceutically effective amount of a mixed extract of Cibotii Rhizoma, Ledebouriellae Radix, Achyranthis Radix, *Paeonia lactiflora* Pall, and Glycyrrhizae Radix, and the mixed extract of Cibotii Rhizoma, Ledebouriellae Radix, Achyranthis Radix, *Paeonia lactiflora* Pall, and Glycyrrhizae Radix increased the survival rate of macrophages in vitro, decreased NO production effectively, exhibited significant inflammatory response-inhibitory effect by inhibiting all of COX-2, iNOS and MMP expressions, showed nerve cell regenerative and protective effects, exhibited pain-inhibitory effect and arthritis edema-inhibitory effect in vivo, and showed disc volume decrease and absorption effect in patients of disc diseases, and thus, the mixed extract of Cibotii Rhizoma, Ledebouriellae Radix, Achyranthis Radix, *Paeonia lactiflora* Pall, and Glycyrrhizae Radix could be used effectively for methods for treating inflammation, arthritis, or disc diseases.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
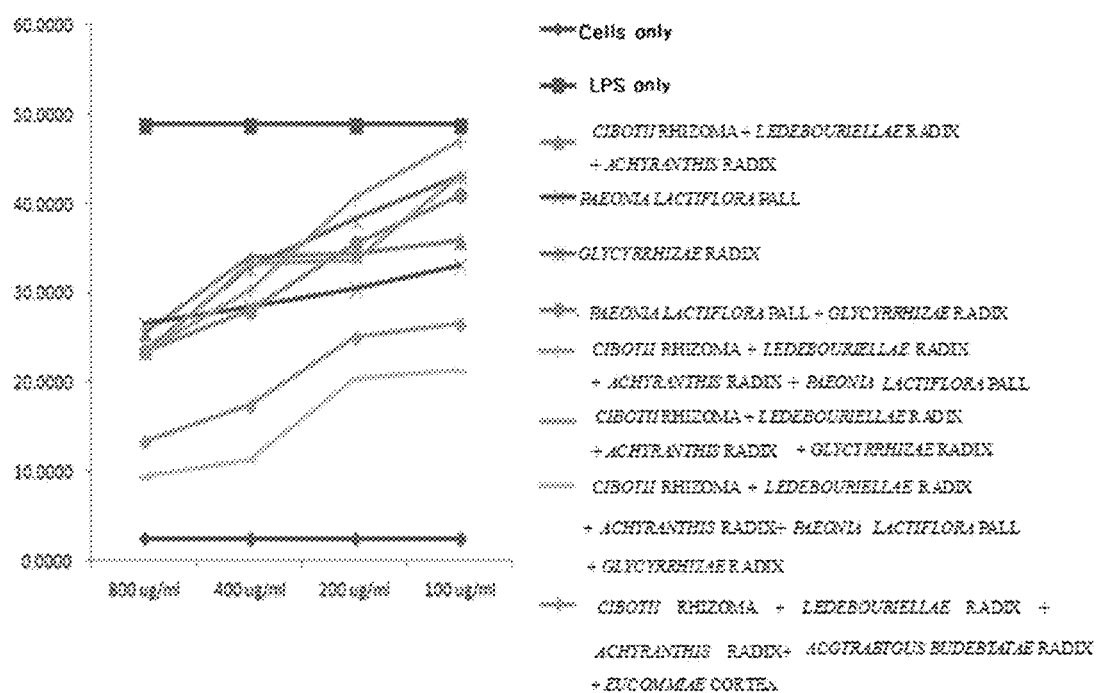
FIG. 1 is a graph illustrating the effect of the mixed extract of Cibotii Rhizoma, Ledebouriellae Radix, Achyranthis Radix, *Paeonia lactiflora* Pall, and Glycyrrhizae Radix on the survival rate of Raw 264.7 cells in which inflammation was induced by LPS.

Hereinafter, the present invention will be described in detail.

The present invention provides a method for treating inflammation, arthritis, or disc diseases, comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

The mixed extract of Cibotii Rhizoma, Ledebouriellae Radix, Achyranthis Radix, *Paeonia lactiflora* Pall, and Glycyrrhizae Radix may be prepared by, but not limited to, a preparation method comprising the following steps of:

(1) adding an extraction solvent to Cibotii Rhizoma, Ledebouriellae Radix, Achyranthis Radix, *Paeonia lactiflora* Pall, and Glycyrrhizae Radix and extracting extract of Cibotii Rhizoma, Ledebouriellae Radix, Achyranthis Radix, *Paeonia lactiflora* Pall, and Glycyrrhizae Radix;

(2) cooling and filtering the extract in step (1); and (3) concentrating the filtered extract in step (2) under reduced pressure and drying the concentrated extract.

In the above method, the extraction solvent in step (1) may be water, a lower alcohol of $C_1$ to $C_2$, or a mixture thereof. The lower alcohol may be, but not limited to, ethanol or methanol. The amount of the extraction solvent may be from about 0.1-fold to about 10-fold, preferably from about 0.3-fold to about 5-fold of the amount of dried Cibotii Rhizoma, Ledebouriellae Radix, Achyranthis Radix, *Paeonia lactiflora* Pall, and Glycyrrhizae Radix, but the present invention is not limited thereto. Extraction temperature may be, but not limited to, from about 20 to about 70° C. Extraction time may be, but not limited to, from about 12 to about 48 hr.

In the above method, concentration under reduced pressure in step (3) may use, but not limited to, a vacuum reduced pressure concentrator or vacuum rotary evaporator. Drying may be, but not limited to, reduced pressure drying, vacuum drying, boiling drying, spray drying, or freeze drying.

The mixed extract may be obtained by mixing Cibotii Rhizoma, Ledebouriellae Radix, Achyranthis Radix, *Paeonia lactiflora* Pall, and Glycyrrhizae Radix and then extracting them, and the respective extracts of Cibotii Rhizoma, Ledebouriellae Radix, Achyranthis Radix, *Paeonia lactiflora* Pall, and Glycyrrhizae Radix may be mixed to use, but the present invention is not limited thereto.

Cibotii Rhizoma, Ledebouriellae Radix, Achyranthis Radix, *Paeonia lactiflora* Pall, and Glycyrrhizae Radix may be mixed at a weight ratio of 1 to 2:1 to 2:1 to 2:1 to 2, respectively, and preferably, at a weight ratio of 1:1.5:1.5:1.5:1.5.

The mixed extract could inhibit NO production and could inhibit expressions of cyclooxygenase-2 (COX-2) and MMPs.

The mixed extract may also have pain-inhibitory, edema-inhibitory, nerve cell regenerative and nerve cell protective effects.

The inflammatory response means the occurrence of a series of complex physiological responses such as enzyme activation by various inflammation mediators and immune cells, release of inflammation mediating substances, body fluid infiltration, cell migration, tissue destruction, etc., stimulated by injuries or external materials such as bacteria, fungi, viruses, etc., and involves symptoms such as erythema, edema, fever and pains. The inflammatory response functions to remove external sources of infection, regenerate injured tissues, and recover functions of organism. However, excessive or continuous inflammatory responses induced by unremoved antigen or internal cause material leads to destruction of mucosa, tissue destruction, and can cause diseases such as cancer, inflammatory skin diseases, inflammatory enteric diseases, arthritis, etc.

Arthritis refers to joint inflammation, often involves pain, stiffness and edema, and its causes are degenerative changes, abnormality of immune system, infection, wound, disturbances of metabolism, etc., and there are more than one hundred kinds. Among them, osteoarthritis and rheumatoid arthritis (RA) account for 80% of the entire arthritis, and make up the largest part of burden caused by musculoskeletal diseases. When dividing factors associated with the onset of osteoarthritis into large groups, proteolytic enzymes, cytokines, and nitric oxide (NO) are known to be main factors. The process of metabolism in cartilage tissues plays a pivotal role in the degeneration of cartilage tissues, and representatively, matrix metalloproteinases (MMPs) are a proteolytic enzyme that destroys matrix components in bone and cartilage, and are expressed also in a pathological condition such as arthritis, and it has been known that MMPs play a major role in etiology. Upon the onset of arthritis, MMPs of which expression increases are MMP-1, MMP-2, MMP-3, MMP-8, MMP-9, MMP-7, and MMP-13, and in particular, it was reported that in cases of MMP-7 and MMP-13, their expression is increased in osteoarthritis.

The arthritis may be, but not limited to, any one selected from the group consisting of osteoarthritis, Rheumatoid arthritis, ankylosing spondylitis, reactive arthritis, psoriatic arthritis, Systemic lupus erythematosus, polymyositis, and polymyalgia rhematica.

In particular examples of the present invention, in order to examine effects of the mixed extract of Cibotii Rhizoma, Ledebouriellae Radix, Achyranthis Radix, *Paeonia lactiflora* Pall, and Glycyrrhizae Radix on inflammation, arthritis, and disc diseases, the present inventors prepared the mixed extract of Cibotii Rhizoma, Ledebouriellae Radix, Achyranthis Radix, *Paeonia lactiflora* Pall, and Glycyrrhizae Radix.

Also, in order to examine cytotoxicity of the mixed extract of Cibotii Rhizoma, Ledebouriellae Radix, Achyranthis Radix, *Paeonia lactiflora* Pall, and Glycyrrhizae Radix of the present invention, the present inventors measured the cell survival rate, and consequently, and consequently, found that the cell survival rate of the cells to which the mixed extract of Cibotii Rhizoma, Ledebouriellae Radix, Achyranthis Radix, *Paeonia lactiflora* Pall, and Glycyrrhizae Radix was treated was higher than that of the cells to which the extract in which one or two or more herbs were mixed was treated (see Table 1 and FIG. 1).

Figure 2:
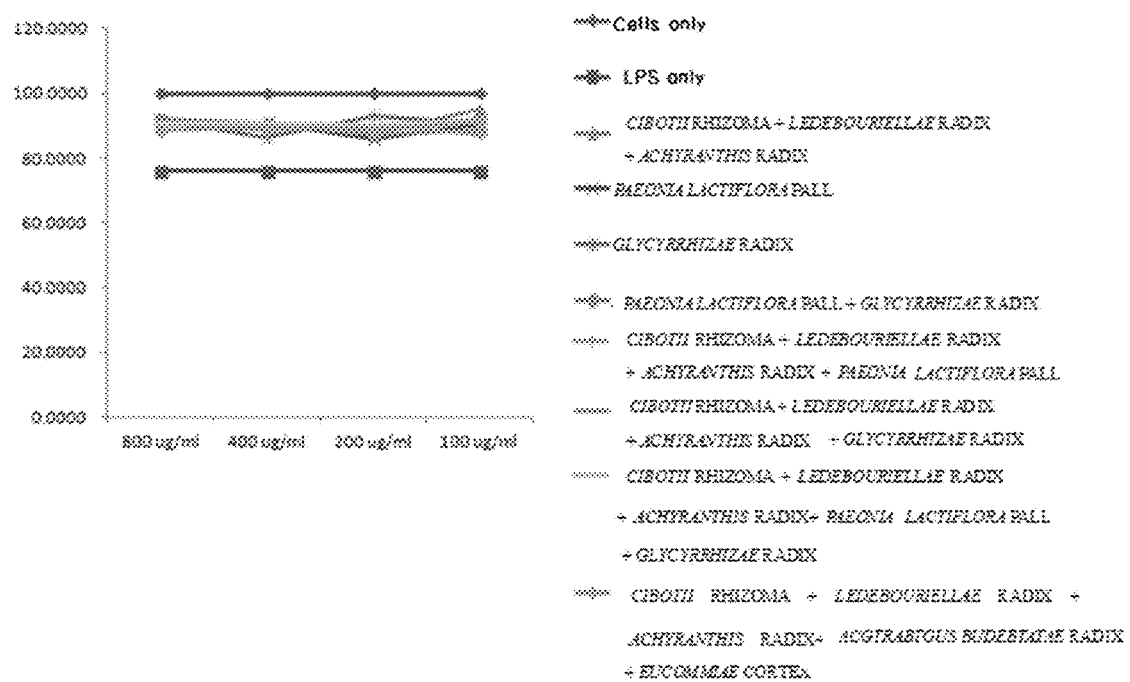
FIG. 2 is a graph illustrating the effect of the mixed extract of Cibotii Rhizoma, Ledebouriellae Radix, Achyranthis Radix, *Paeonia lactiflora* Pall, and Glycyrrhizae Radix on the NO production of Raw 264.7 cells in which inflammation was induced by LPS.

The present inventors also measured NO production caused by treatment of the extract of Cibotii Rhizoma, Ledebouriellae Radix, Achyranthis Radix, *Paeonia lactiflora* Pall, and Glycyrrhizae Radix, and consequently, found that NO production in cells treated with the mixed extract of the present invention decreased effectively, two or more times as much as NO production in cells treated with the extract of one or two or more mixed herbs (see Table 2 and FIG. 2).

Figure 3:
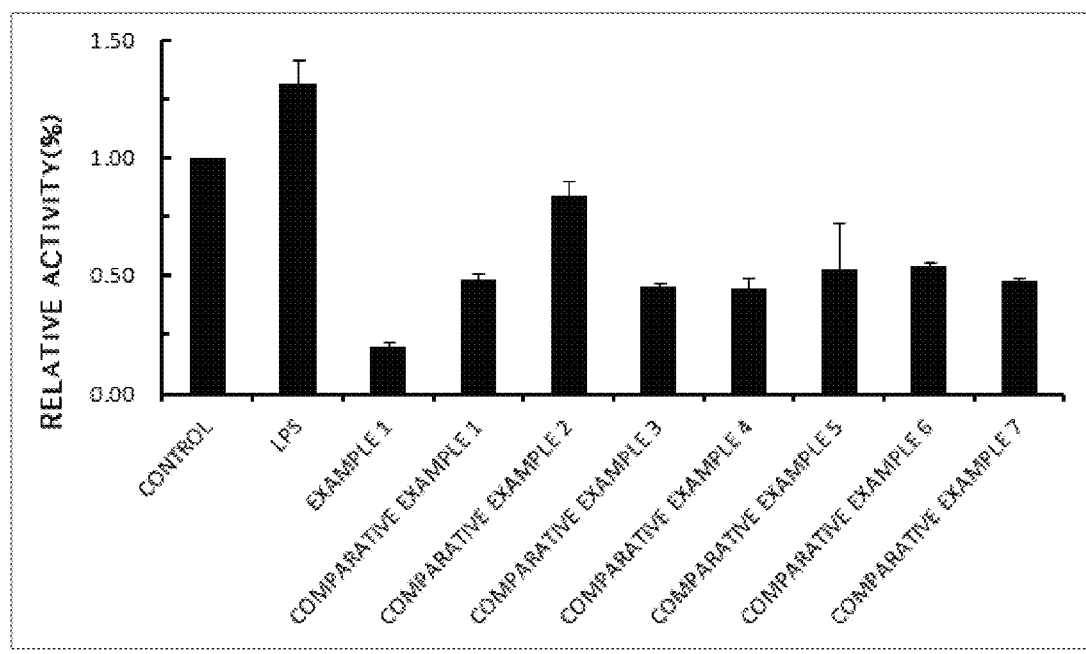
FIG. 3 shows that COX-2 expression was effectively inhibited by treating articular synovial cells in which inflammation was induced by LPS with the mixed extract of Cibotii Rhizoma, Ledebouriellae Radix, Achyranthis Radix, *Paeonia lactiflora* Pall, and Glycyrrhizae Radix.

Also, the present inventors measured COX-2 expression in order to examine the effect of the mixed extract of Cibotii Rhizoma, Ledebouriellae Radix, Achyranthis Radix, *Paeonia lactiflora* Pall, and Glycyrrhizae Radix of the present invention on the expression of an inflammatory cytokine, COX-2, which is a marker for osteoarthritis, in vitro, and consequently, found that COX-2 expression in cells treated with the extract of the present invention was inhibited 2.5 times more effectively than the COX-2 expressions in cells treated with the extract of one or two or more mixed herbs (see FIG. 3).

Figure 4:
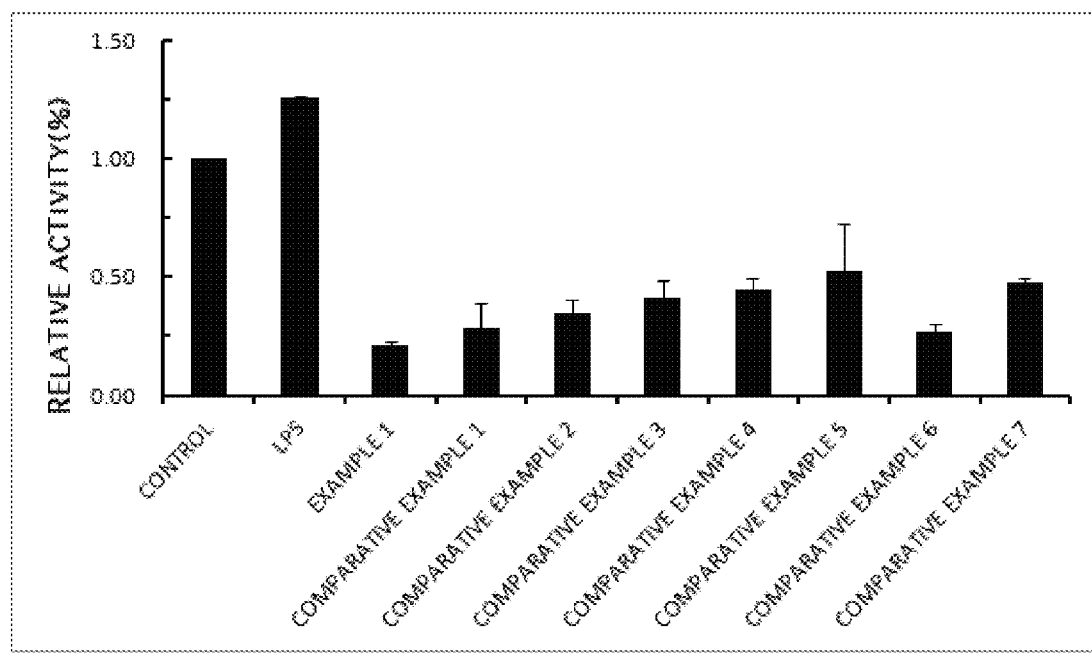
FIG. 4 shows that iNOS expression was effectively inhibited by treating articular synovial cells in which inflammation was induced by LPS with the mixed extract of Cibotii Rhizoma, Ledebouriellae Radix, Achyranthis Radix, *Paeonia lactiflora* Pall, and Glycyrrhizae Radix.

In addition, the present inventors measured iNOS expression in order to examine the effect of the mixed extract of Cibotii Rhizoma, Ledebouriellae Radix, Achyranthis Radix, *Paeonia lactiflora* Pall, and Glycyrrhizae Radix of the present invention on the expression of inducible nitric oxide synthetase (iNOS), which is a marker for osteoarthritis, and consequently, found that iNOS expression in cells treated with the extract of the present invention was inhibited more effectively than the iNOS expressions in cells treated with the extract of one or two or more mixed herbs (see FIG. 4).

Figure 5:
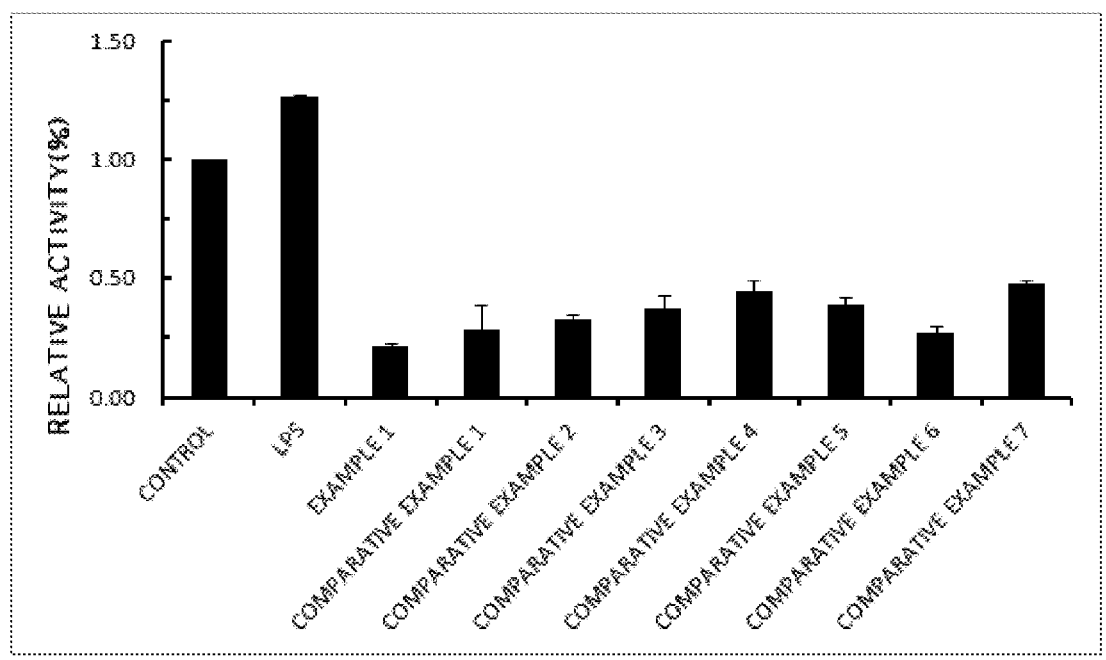
FIG. 5 shows that MMP expression was effectively inhibited by treating articular synovial cells in which inflammation was induced by LPS with the mixed extract of Cibotii Rhizoma, Ledebouriellae Radix, Achyranthis Radix, *Paeonia lactiflora* Pall, and Glycyrrhizae Radix.

Further, the present inventors measured MMP-13 expression in order to examine the effect of the mixed extract of Cibotii Rhizoma, Ledebouriellae Radix, Achyranthis Radix, *Paeonia lactiflora* Pall, and Glycyrrhizae Radix of the present invention on the expression of MMP-13, which is a marker for osteoarthritis, and consequently, found that MMP-13 expression in cells treated with the mixed extract of the present invention was inhibited more remarkably than the MMP-13 expressions in cells treated with the extract of one or two or more mixed herbs (see FIG. 5).

The present inventors also measured the number of pains (writhing) (Koster et al., 1959) in order to examine the pain-inhibitory effect of the mixed extract of Cibotii Rhizoma, Ledebouriellae Radix, Achyranthis Radix, *Paeonia lactiflora* Pall, and Glycyrrhizae Radix of the present invention in vivo, and consequently, the number of pains in the group to which the mixed extract of the present invention was administered was smaller than that of the group to which the extract of one or two or more mixed herbs was administered, and similar to the positive control group to which phenylbutazone was administered (see Table 6).

In addition, the present inventors measured foot volume of edema-induced white rats in order to examine the arthritis edema-inhibitory effect of the mixed extract of Cibotii Rhizoma, Ledebouriellae Radix, Achyranthis Radix, *Paeonia lactiflora* Pall, and Glycyrrhizae Radix of the present invention in vivo, and calculated edema inhibition rate in order to measure edema increase rate in white rats to which the mixed extract was administered, and consequently, found that edema was induced since $4^{th}$ day in arthritis edema-induced rats and Zusanli edema in white rats to which the mixed extract was administered was remarkably reduced compared to edema in white rats to which one or two or more mixed herbs was administered (see Table 7).

Figure 6:
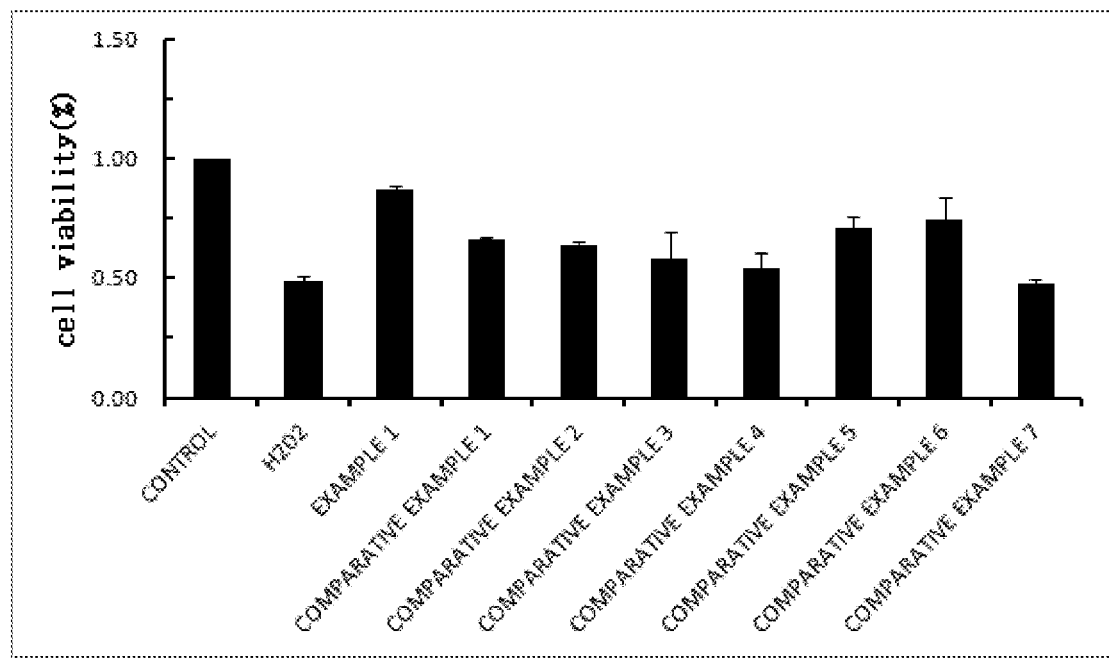
FIG. 6 shows that when PC12 cells were treated with the mixed extract of Cibotii Rhizoma, Ledebouriellae Radix, Achyranthis Radix, *Paeonia lactiflora* Pall, and Glycyrrhizae Radix, the cells' survival rate was high.

Further, the present inventors measured the cell survival rate in order to examine the nerve cell regenerative effect of the mixed extract of Cibotii Rhizoma, Ledebouriellae Radix, Achyranthis Radix, *Paeonia lactiflora* Pall, and Glycyrrhizae Radix of the present invention, and consequently, found that the cell survival rate of the cells to which the mixed extract of the present invention was treated was at least two times higher than that of the cells to which the extract in which one or two or more herbs were mixed was treated (see FIG. 6).

Figure 7:
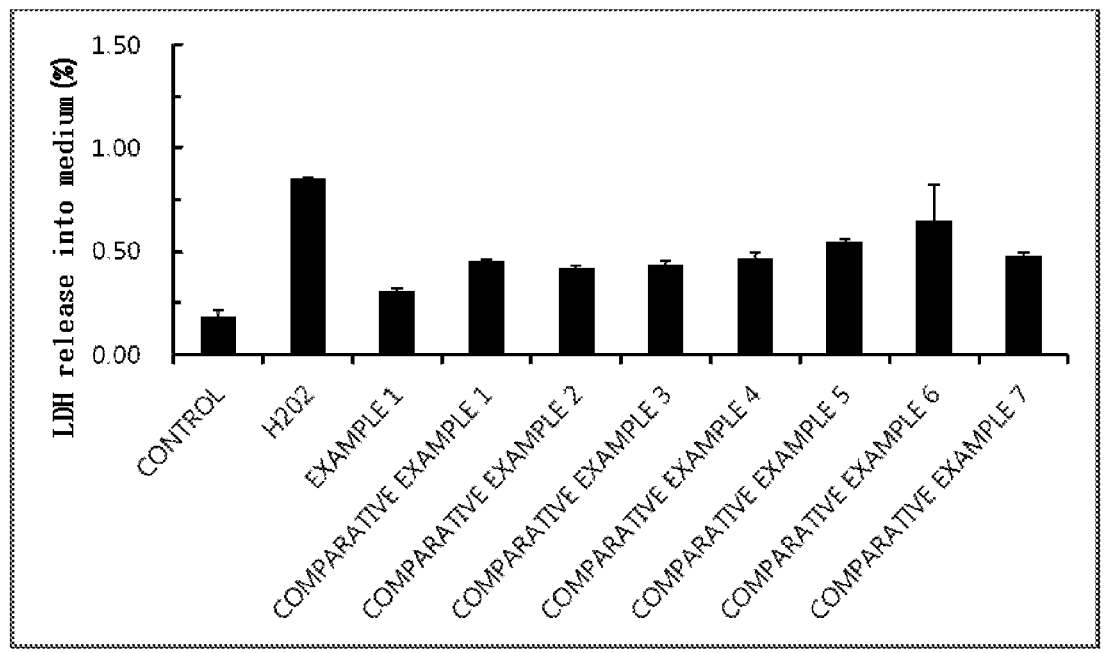
FIG. 7 shows that when PC12 cells in which cell membrane damage was caused by $H_2O_2$ were treated with the mixed extract of Cibotii Rhizoma, Ledebouriellae Radix, Achyranthis Radix, *Paeonia lactiflora* Pall, and Glycyrrhizae Radix, LDH release decreased.

The present inventors also measured LDH release in order to examine the cell membrane damage protective effect of the mixed extract of Cibotii Rhizoma, Ledebouriellae Radix, Achyranthis Radix, *Paeonia lactiflora* Pall, and Glycyrrhizae Radix of the present invention, and consequently, found that LDH release of the cell membrane of the cells to which the extract of the present invention was reduced 1.5 times more than that of the cells to which the extract in which one or two or more herbs were mixed was treated (see FIG. 7). Thus, it was found that the mixed extract of the present invention had nerve cell protective effect.

Figure 8:
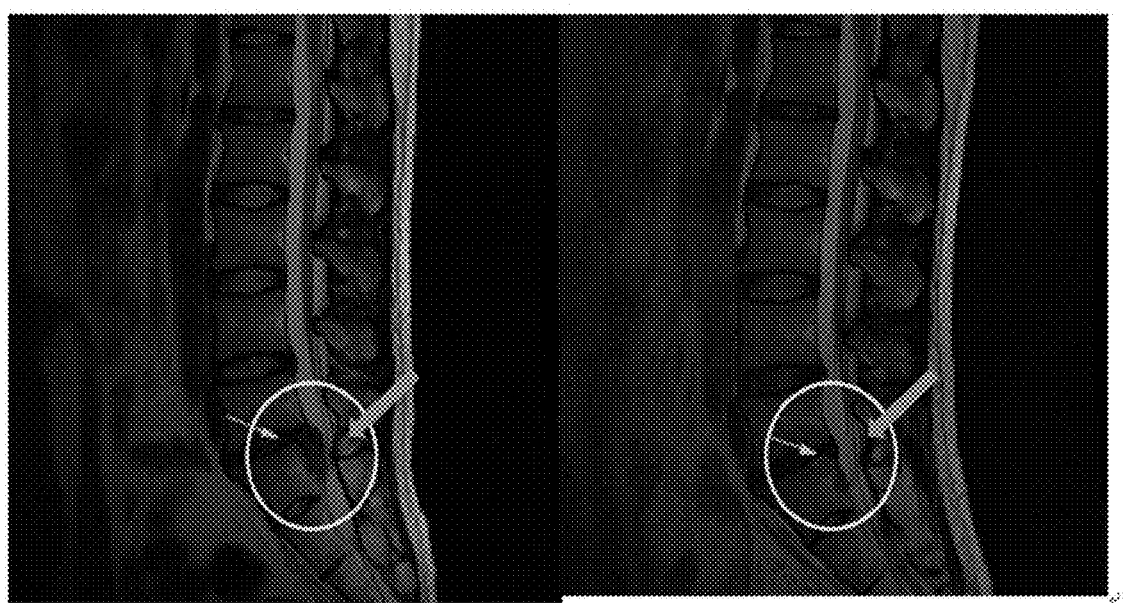
FIG. 8 shows a result of the MRI scan of patient 1 with disc disease taken the mixed extract of Cibotii Rhizoma, Ledebouriellae Radix, Achyranthis Radix, *Paeonia lactiflora* Pall, and Glycyrrhizae Radix for 6 months.
Figure 9:
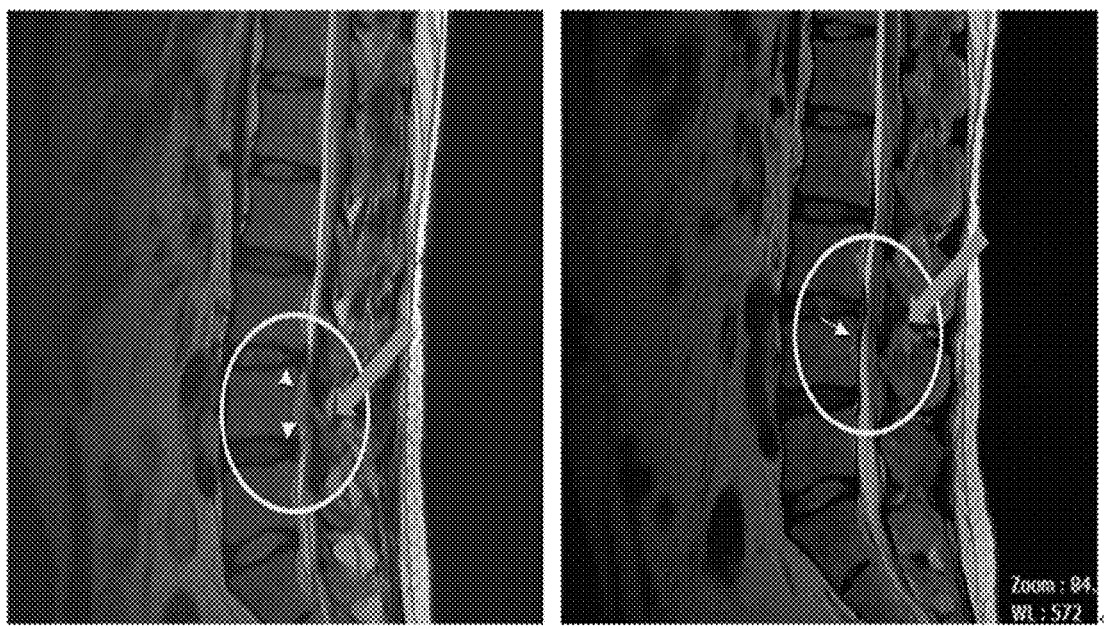
FIG. 9 shows a result of the MRI scan of patient 2 with disc disease taken the mixed extract of Cibotii Rhizoma, Ledebouriellae Radix, Achyranthis Radix, *Paeonia lactiflora* Pall, and Glycyrrhizae Radix for 6 months.
Figure 10:
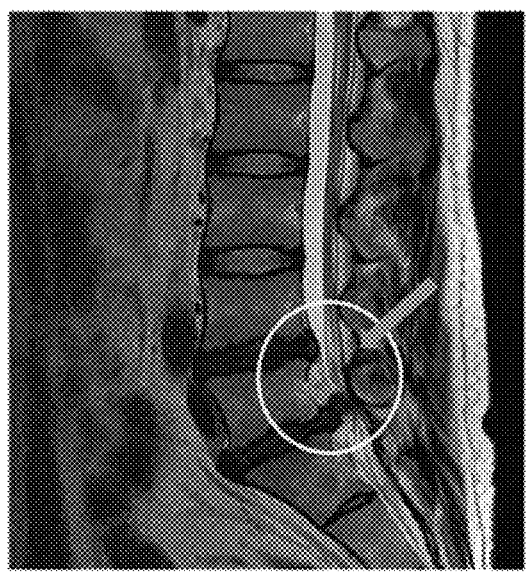
FIG. 10 shows a result of the MRI scan of patient 3 with disc disease taken the mixed extract of Cibotii Rhizoma, Ledebouriellae Radix, Achyranthis Radix, *Paeonia lactiflora* Pall, and Glycyrrhizae Radix for 6 months.
Figure 10:
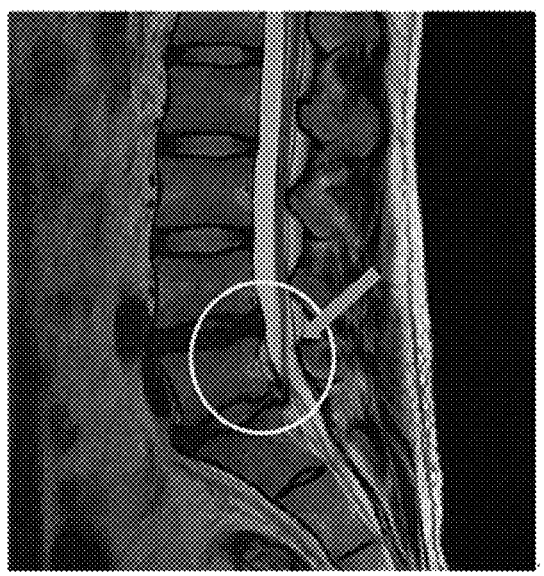
Figure 11:
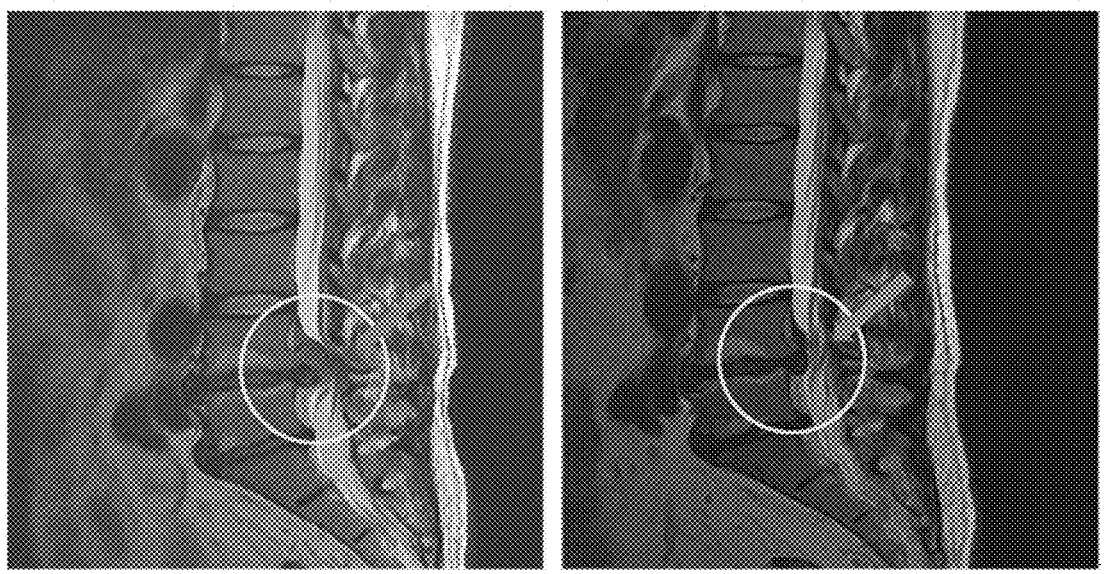
FIG. 11 shows a result of the MRI scan of patient 4 with disc disease taken the mixed extract of Cibotii Rhizoma, Ledebouriellae Radix, Achyranthis Radix, *Paeonia lactiflora* Pall, and Glycyrrhizae Radix for 6 months.

In addition, the present inventors performed MRI in order to examine clinical pharmacological effects of the mixed extract of Cibotii Rhizoma, Ledebouriellae Radix, Achyranthis Radix, *Paeonia lactiflora* Pall, and Glycyrrhizae Radix of the present invention, and consequently, found that different disc symptoms were found from all five patients (see Table 8). Then, after administering the extract for 6 months, the effect of the mixed extract of the present invention on disc patients was examined using MRI. Decrease in extruded disc volume and improvement in the degree of neuromembrane and nerve-root compression were observed (see FIG. 8), absorption of extruded disc and decrease in extruded disc volume were observed (see FIG. 9, FIG. 10, and FIG. 11), and decrease in sequestered disc volume and absorption of the sequestered disc were observed (see FIG. 12). Accordingly, from the experimental result, it was found that the mixed extract of Cibotii Rhizoma, Ledebouriellae Radix, Achyranthis Radix, *Paeonia lactiflora* Pall and Glycyrrhizae Radix could reduce and absorb effectively the disc volume in disc patients.

Thus, the mixed extract of Cibotii Rhizoma, Ledebouriellae Radix, Achyranthis Radix, *Paeonia lactiflora* Pall and Glycyrrhizae Radix of the present invention increased the survival rate of macrophages in vitro, inhibited the production of NO, which is involved in anti-inflammation, inhibited COX-2, iNOS and MMP expressions, decreased LDH expression to prove nerve cell regenerative and protective effects, inhibited pain and arthritis edema in vivo, and exhibited the disc volume-reducing and absorbing effects in patients of disc diseases. Accordingly, the mixed extract of Cibotii Rhizoma, Ledebouriellae Radix, Achyranthis Radix, *Paeonia lactiflora* Pall and Glycyrrhizae Radix of the present invention can be used effectively for a method for treating inflammation, arthritis, or disc diseases.

A composition comprising the mixed extract of Cibotii Rhizoma, Ledebouriellae Radix, Achyranthis Radix, *Paeonia lactiflora* Pall and Glycyrrhizae Radix of the present invention may further contain one or more kinds of active ingredients having the same or similar function, in addition to the ingredient.

The composition of the present invention may further comprise a pharmaceutically acceptable additive, and the pharmaceutically acceptable additive may be starch, gelatinized starch, microcrystalline cellulose, lactose, povidone, colloidal silicon dioxide, calcium hydrogen phosphate, lactose, mannitol, taffy, Arabia rubber, pregelatinized starch, corn starch, cellulose powder, hydroxypropyl cellulose, Opadry, sodium starch glycolate, carunauba wax, synthetic aluminum silicate, stearic acid, magnesium stearate, aluminum stearate, calcium stearate, white sugar, dextrose, sorbitol, talc, etc. The pharmaceutically acceptable additive according to the present invention may be added by 0.1-90 parts by weight to the composition, but the present invention is not limited thereto.

That is, the composition of the present invention may be administered as various oral or parenteral formulations upon practical clinical administration. Formulations may prepared by using diluents or excipients such as fillers, extenders, binders, humectants, disintegrators, surfactants, etc. that are generally used.

Solid formulations for oral administration include tablets, pills, powders, granules, capsules, etc. and these solid formulations may be prepared by mixing at least one or more excipients, for example, starch, calcium carbonate, sucrose, lactose, or gelatin with the extract. Also, lubricants such as magnesium stearate, talc, etc. may be used in addition to simple excipients. Liquid formulations for oral administration include suspensions, liquid for internal use, emulsions, syrups, etc., and various excipients such as humectants, sweeteners, aromatics, preservatives, etc. in addition to generally-used simple diluents such as water and liquid paraffin may be included. Formulations for parenteral administration may include sterile aqueous solutions, non-aqueous solvents, suspensions, emulsions, freeze-dried formulations, and suppositories. Propylene glycol, polyethylene glycol, vegetable oil such as olive oil, and injectable ester such as ethylolate, etc. may be used for non-aqueous solvents and suspensions. Witepsol, macrogol, tween 61, cacao butter, laurin butter, glycerogelatin, etc. may be used for a suppository base.

The composition of the present invention may be administered orally or parenterally depending on a purposeful method. For parental administration, external application or intraperitoneal injection, rectal injection, hypodermic injection, intravenous injection, intramuscular injection, or intrathoracic injection may be selected. The administration dose may vary depending on body weight, age, gender, health condition, diet of a certain patient, administration period, administration method, clearance, severity of a disease, etc.

The composition according to the present invention is administered in a pharmaceutically effective amount. As used herein, the term "pharmaceutically effective amount" refers to a sufficient amount to treat a disease at a reasonable benefit/risk ratio applicable for medical treatment, and an effective dose level can be determined by factors including the kind of patient's disease, severity, activity of a drug, sensitivity to a drug, administration time, administration route and excretion ratio, duration of treatment and other drugs to be concurrently used, and other factors well known in the medical field. The composition of the present invention may be administered as an individual therapeutic agent or in combination with other therapeutic agents, may be administered sequentially or concurrently with existing therapeutic agents, or may be administered in a singular or multiple doses. It is essential to administer in an amount capable of obtaining maximum effects with a minimum amount without incurring any side-effects in light of all the above listed factors, and it can be easily determined by those skilled in the art.

In particular, the effective amount of the compound in accordance with the present invention may vary by the age, gender and weight of patients and in general, 0.01 to 1000 mg, preferably 0.1 to 100 mg per kg of body weight may be administered daily or on every other day, ranging from one to three times per day. However, since this may be increased or decreased in light of the route of administration, the severity of obesity, gender, weight, age, etc., it should be understood that the dosage suggested above does not limit the scope of the invention in any way.

The composition of the present invention may be used alone, or in combination with surgery, radiation therapy, hormone therapy, chemotherapy, and methods using biological response modifiers.

The present invention also provides a method for regenerating nerve cells comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

Furthermore, the present invention provides a method for protecting nerve cells comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

It was found that the cell survival rate of the cells to which the mixed extract of Cibotii Rhizoma, Ledebouriellae Radix, Achyranthis Radix, *Paeonia lactiflora* Pall, and Glycyrrhizae Radix of the present invention was treated was higher than that of the cells to which the extract in which one or two or more herbs were mixed was treated, and LDH release was reduced in the cell membrane of the cells to which the mixed extract of the present invention was treated, and thus, the mixed extract of the present invention can be used for the method for regenerating or protecting nerve cells comprising administering to an individual the extract of Cibotii Rhizoma, Ledebouriellae Radix, Achyranthis Radix, *Paeonia lactiflora* Pall, and Glycyrrhizae Radix.

The present invention also provides a treatment method of inhibiting arthritis edema comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

Edema refers to the condition in which fluid in capillaries escapes from blood vessels and is trapped in the interstitial tissue, the phenomenon in which tissues are expanded due to increased interstitial fluid, and the result of salts and water retention.

Edema is observed when interstitial volume increases by at least 2.5 to 3 L. Edema appears often on the face, chest, abdomen, limbs, or whole body, and can be classified into local edema and systemic edema depending on internal distribution. Its causative diseases are renal diseases, heart diseases, liver diseases, some women's diseases (idiopathic edema, edema involved in pregnancy or menstruation), gastrointestinal diseases, endocrine diseases (thyroid disease, adrenal cortex diseases, and diabetes mellitus), lymphedema, skin diseases, etc. Patients having arthritis often experience synovitis, increase in joint fluid, deformation of bone and joint, pains due to joint wear including swollen joints, and walking difficulty due to the surrounding soft tissue swelling-induced compression. When the patient gains body weight due to other diseases, in particular, edema, the pressure applied to joint increases.

The arthritis may be, but not limited to, any one selected from the group consisting of osteoarthritis, Rheumatoid arthritis, ankylosing spondylitis, reactive arthritis, psoriatic arthritis, Systemic lupus erythematosus, polymyositis, and polymyalgia rhematica.

Cibotii Rhizoma, Ledebouriellae Radix, Achyranthis Radix, *Paeonia lactiflora* Pall, and Glycyrrhizae Radix may be mixed at a weight ratio of 1 to 2:1 to 2:1 to 2:1 to 2:1 to 2, respectively, and preferably, at a weight ratio of 1:1.5:1.5:1.5:1.5.

The mixed extract may be obtained by using water, a lower alcohol of $C_1$ to $C_2$, or a mixture thereof as a solvent, and the lower alcohol may be ethanol or methanol.

Since when the extract of Cibotii Rhizoma, Ledebouriellae Radix, Achyranthis Radix, *Paeonia lactiflora* Pall, and Glycyrrhizae Radix was administered to edema-induced white rats, the extract of Cibotii Rhizoma, Ledebouriellae Radix, Achyranthis Radix, *Paeonia lactiflora* Pall, and Glycyrrhizae Radix of the present invention showed 1.5 times higher edema-inhibitory effect than the edema inhibition rate of white rats administered with the extract of one or two or more mixed herbs, the mixed extract of the present invention can be used effectively for the treatment method of inhibiting arthritis edema comprising administering to an individual the extract of Cibotii Rhizoma, Ledebouriellae Radix, Achyranthis Radix, *Paeonia lactiflora* Pall, and Glycyrrhizae Radix.

The present invention also provides a method of inhibiting inflammation comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

Furthermore, the present invention provides a treatment method for inhibiting pain comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

The present invention also provides a method of inhibiting inflammatory pain comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

Inflammation is a series of syndromes, involving edema, hot sensation, pains, etc., by blood vessel expansion, blood exudation, inflammatory cell migration, sensitization of algesireceptor, etc. In humans, rheumatoid arthritis, bacterial infection, and other inflammatory diseases are known to be important factors in chronic pain sensory. In the process of inflammation response, inflammation-inducible materials (e.g., interleukin-1, tumor necrosis factor, lipopolysaccharide etc.) promote the expression of an enzyme which produces NO using L-arginine as a substrate, nitric oxide synthase (NOS) being released, and eventually, increase NO production (Brdt et al., 1992; Lafond-Walker et al., 1997; Lowenstein et al., 1994). This NO has been reported to be involved in induction of pain sensation. That is, it was observed that when NO production was inhibited by administering a NOS antagonist, the degree of inflammation was reduced and the accelerated neural activity caused by inflammation was also reduced (Haley et al., 1992; Roche et al., 1996). The above result suggests that NO is involved in inflammation induction as well as pain induction.

Cibotii Rhizoma, Ledebouriellae Radix, Achyranthis Radix, *Paeonia lactiflora* Pall, and Glycyrrhizae Radix may be mixed at a weight ratio of 1 to 2:1 to 2:1 to 2:1 to 2, respectively, and preferably, at a weight ratio of 1:1.5:1.5:1.5:1.5.

The mixed extract may be obtained by using water, a lower alcohol of $C_1$ to $C_2$, or a mixture thereof as a solvent, and the lower alcohol may be ethanol or methanol.

The mixed extract could inhibit NO production and could inhibit expressions of cyclooxygenase-2 (COX-2) and MMPs.

The mixed extract may also have pain-inhibitory, edema-inhibitory, nerve cell regenerative and nerve cell protective effects.

Thus, since the mixed extract of Cibotii Rhizoma, Ledebouriellae Radix, Achyranthis Radix, *Paeonia lactiflora* Pall and Glycyrrhizae Radix of the present invention increased the survival rate of macrophages in vitro, inhibited the production of NO, which is involved in anti-inflammation, inhibited COX-2, iNOS and MMP expressions, and inhibited pain and arthritis edema in vivo, it can be used effectively for the method of inhibiting inflammation, pain or inflammatory pain comprising administering to an individual the mixed extract of Cibotii Rhizoma, Ledebouriellae Radix, Achyranthis Radix, *Paeonia lactiflora* Pall, and Glycyrrhizae Radix.

The present invention also provides a method for treating disc diseases comprising administering to an individual a pharmaceutically effective amount of a mixed extract of Cibotii Rhizoma, Ledebouriellae Radix, Achyranthis Radix, *Paeonia lactiflora* Pall, and Glycyrrhizae Radix.

In a human body, when a disc between vertebrae, i.e., an intervertebral disc ages, circumferential fissure and radial tear occur in a fibrous ring which surrounds the border of intervertebral disc. At the time, where compression force and twisting force are applied to the spine in an excessively bent state, nucleus pulposus in the middle of the intervertebral disc cannot be surrounded by the fibrous ring and leaks through radial tears, causing so called lumbar herniated intervertebral disc. This condition is generally referred to as disc or degenerative disc disease, and is classified into lumbar disc and cervical disc depending on the part of occurrence.

Cibotii Rhizoma, Ledebouriellae Radix, Achyranthis Radix, *Paeonia lactiflora* Pall, and Glycyrrhizae Radix may be mixed at a weight ratio of 1 to 2:1 to 2:1 to 2:1 to 2:1 to 2, respectively, and preferably, at a weight ratio of 1:1.5:1.5:1.5:1.5.

The mixed extract may be obtained by using water, a lower alcohol of $C_1$ to $C_2$, or a mixture thereof as a solvent, and the lower alcohol may be ethanol or methanol.

Since decrease in extruded disc volume, improvement in the degree of neuromembrane and nerve-root compression, absorption of extruded disc, decrease in extruded disc volume, decrease in sequestered disc volume and absorption were observed in disc disease patients who administered the mixed extract of Cibotii Rhizoma, Ledebouriellae Radix, Achyranthis Radix, *Paeonia lactiflora* Pall, and Glycyrrhizae Radix, the mixed extract of the present invention can be used effectively for the method for treating disc comprising administering to an individual the extract of Cibotii Rhizoma, Ledebouriellae Radix, Achyranthis Radix, *Paeonia lactiflora* Pall, and Glycyrrhizae Radix.

The present invention also provides anti-inflammation, prevention of arthritis or disc diseases, and a pharmaceutical composition, or a health food for improvement of arthritis or disc diseases, containing a mixed extract of Cibotii Rhizoma, Ledebouriellae Radix, Achyranthis Radix, *Paeonia lactiflora* Pall, and Glycyrrhizae Radix as an active ingredient.

Furthermore, the present invention provides prevention of arthritis edema, and a pharmaceutical composition, or a health food for improvement of arthritis edema, containing a mixed extract of Cibotii Rhizoma, Ledebouriellae Radix, Achyranthis Radix, *Paeonia lactiflora* Pall, and Glycyrrhizae Radix as an active ingredient.

The present invention also provides prevention of disc diseases, and a pharmaceutical composition, or a health food for improvement of disc diseases, containing a mixed extract of Cibotii Rhizoma, Ledebouriellae Radix, Achyranthis Radix, *Paeonia lactiflora* Pall, and Glycyrrhizae Radix as an active ingredient.

Furthermore, the present invention provides prevention of inflammatory pain, and a pharmaceutical composition, or a health food for improvement of inflammatory pain, containing a mixed extract of Cibotii Rhizoma, Ledebouriellae Radix, Achyranthis Radix, *Paeonia lactiflora* Pall, and Glycyrrhizae Radix as an active ingredient.

Cibotii Rhizoma, Ledebouriellae Radix, Achyranthis Radix, *Paeonia lactiflora* Pall, and Glycyrrhizae Radix may be mixed at a weight ratio of 1 to 2:1 to 2:1 to 2:1 to 2, respectively, and preferably, at a weight ratio of 1:1.5:1.5:1.5:1.5.

The mixed extract may be obtained by using water, a lower alcohol of $C_1$ to $C_2$, or a mixture thereof as a solvent, and the lower alcohol may be ethanol or methanol.

The mixed extract could inhibit NO production and could inhibit expressions of cyclooxygenase-2 (COX-2) and MMPs.

The mixed extract may also have pain-inhibitory, edema-inhibitory, nerve cell regenerative and nerve cell protective effects.

Thus, since the mixed extract of Cibotii Rhizoma, Ledebouriellae Radix, Achyranthis Radix, *Paeonia lactiflora* Pall and Glycyrrhizae Radix of the present invention increased the survival rate of macrophages in vitro, inhibited the production of NO, which is involved in anti-inflammation, inhibited COX-2, iNOS and MMP expressions, showed nerve cell regenerative and protective effects, inhibited pain and arthritis edema in vivo, and exhibited the disc volume-reducing and absorbing effects in patients of disc diseases, it was found that the mixed extract of Cibotii Rhizoma, Ledebouriellae Radix, Achyranthis Radix, *Paeonia lactiflora* Pall and Glycyrrhizae Radix can be used effectively for health foods for prevention or improvement of inflammation, arthritis, or disc diseases.

There is no particular limitation as to the kind of food. Examples of foods to which the extract can be added include meats, sausages, breads, chocolates, candies, snacks, confectionery, pizzas, instant noodles, other noodles, gum, dairy products including ice creams, a variety of soups, beverages, teas, drinks, alcohol beverages, and vitamin complexes, etc. and include all health foods in the conventional meaning.

In a case that the mixed extract of the present invention is used as a food additive, the extract may be added as it is or be mixed to use with other foods or food ingredients, and may be used according to a conventional method. The mixing ratio of active ingredients can be determined according to the purpose of use (prevention, health or therapeutic treatment). In general, the amount of the extract to be added to the health food may be 0.1 to 90 parts by weight to the weight of the whole health food. However, if long term administration is required for health and hygiene or regulating health condition, the amount can be lower than the above but higher amount can be accepted as well since the active ingredient has been proved to be very safe.

A healthy beverage composition of the present invention may comprise various flavors or natural carbohydrates, etc. as an additional ingredient like conventional beverages. The natural carbohydrate may be monosaccharides such as glucose and fructose, disaccharides such as maltose and sucrose, polysaccharides such as dextrin and cyclodextrin, and sugar alcohols such as xylitol, sorbitol, erythritol, etc. Natural sweeteners such as thaumatin and stevia extract or synthetic sweeteners such as saccharin and aspartame may used for sweeteners. The amount of the natural carbohydrate may be generally about 1 to 20 g, preferably about 5 to 12 g based on 100 g of the composition of the present invention.

In addition to that, the mixed extract of the present invention may contain various nutritional supplements, vitamins, electrolytes, flavors, colorants, pectic acid and its salt, alginic acid and its salt, organic acids, protective colloidal thickeners, pH regulating agents, stabilizers, preservatives, glycerin, alcohols, carbonizing agents used in carbonated drinks, etc. Moreover, the mixed extract of the present invention may contain fruit flesh for the preparation of natural fruit juices, fruit juice beverages, and vegetable beverages. These ingredients may be used alone or in combination.

Hereinafter, the present invention will be described in more detail with reference to Examples.

However, the following examples are provided for illustrative purposes only, and the scope of the present invention should not be limited thereto.

Example 1

Preparation of Water Extract of Cibotii Rhizoma, Ledebouriellae Radix, Achyranthis Radix, *Paeonia lactiflora* Pall, and Glycyrrhizae Radix In the present invention, Cibotii Rhizoma, Ledebouriellae Radix, Achyranthis Radix, *Paeonia lactiflora* Pall, and Glycyrrhizae Radix were purchased from Green Myungpum Pharm. Co., Ltd. (hGMP, Republic of Korea) and were finely cut to use. 100 g of each Cibotii Rhizoma, Ledebouriellae Radix, Achyranthis Radix, *Paeonia lactiflora* Pall, and Glycyrrhizae Radix was prepared to be in a weight ratio of 1:1.5:1.5:1.5:1.5. Water was added ten times as large as the weight of raw herbs to the raw herbs, and hot water extraction was performed at 105° C. for 1 hr. The extract was concentrated by a vacuum concentrator and freeze dried for 1 week under the condition of −80° C., 5 mtorr. The yield of the extract of Cibotii Rhizoma, Ledebouriellae Radix, Achyranthis Radix, *Paeonia lactiflora* Pall, and Glycyrrhizae Radix which was freeze-dried and measured was 8.29% based on the weight of the raw herbs. The extract was prepared to be in a weight ratio of 1:1.5:1.5:1.5:1.5.

Example 2

Preparation of Mixed Ethanol Extract of Cibotii Rhizoma, Ledebouriellae Radix, Achyranthis Radix, *Paeonia lactiflora* Pall, and Glycyrrhizae Radix Cibotii Rhizoma, Ledebouriellae Radix, Achyranthis Radix, *Paeonia lactiflora* Pall, and Glycyrrhizae Radix were mixed and 70% ethanol was added thereto. Then, the mixed ethanol extract of Cibotii Rhizoma, Ledebouriellae Radix, Achyranthis Radix, *Paeonia lactiflora* Pall, and Glycyrrhizae Radix was prepared by the same method in Example <1-1>.

Example 3

Preparation of Mixed Methanol Extract of Cibotii Rhizoma, Ledebouriellae Radix, Achyranthis Radix, *Paeonia lactiflora* Pall, and Glycyrrhizae Radix Cibotii Rhizoma, Ledebouriellae Radix, Achyranthis Radix, *Paeonia lactiflora* Pall, and Glycyrrhizae Radix were mixed and 70% methanol was added thereto. Then, the mixed methanol extract of Cibotii Rhizoma, Ledebouriellae Radix, Achyranthis Radix, *Paeonia lactiflora* Pall, and Glycyrrhizae Radix was prepared by the same method in Example <1-1>.

Comparative Example 1

Preparation of Extract of Cibotii Rhizoma, Ledebouriellae Radix, and Achyranthis Radix By the same extraction method in <Example 1>, 10.11% of hot water extract of Cibotii Rhizoma, Ledebouriellae Radix, and Achyranthis Radix was obtained in comparison with the weight of raw herbs. The extract was prepared to be in a weight ratio of 1:1.5:1.5.

Comparative Example 2

Preparation of Extract of *Paeonia lactiflora* Pall

By the same extraction method in <Example 1>, 9.72% of extract of *Paeonia lactiflora* Pall was obtained in comparison with the weight of raw herb. The extract was prepared to be in a weight ratio of 1.

Comparative Example 3

Preparation of Extract of Glycyrrhizae Radix

By the same extraction method in <Example 1>, 10.00% of extract of Glycyrrhizae Radix was obtained in comparison with the weight of raw herb. The extract was prepared to be in a weight ratio of 1.

Comparative Example 4

Preparation of Extract of *Paeonia lactiflora* Pall and Glycyrrhizae Radix

By the same extraction method in <Example 1>, 9.45% of extract of *Paeonia lactiflora* Pall and Glycyrrhizae Radix was obtained in comparison with the weight of raw herbs. The extract was prepared to be in a weight ratio of 1:1.

Comparative Example 5

Preparation of Extract of Cibotii Rhizoma, Ledebouriellae Radix, Achyranthis Radix, and *Paeonia lactiflora* Pall By the same extraction method in <Example 1>, 10.03% of extract of Cibotii Rhizoma, Ledebouriellae Radix, Achyranthis Radix, and *Paeonia lactiflora* Pall was obtained in comparison with the weight of raw herbs. The extract was prepared to be in a weight ratio of 1:1.5:1.5:1.5.

Comparative Example 6

Preparation of Extract of Cibotii Rhizoma, Ledebouriellae Radix, Achyranthis Radix, and Glycyrrhizae Radix By the same extraction method in <Example 1>, 10.10% of extract of Cibotii Rhizoma, Ledebouriellae Radix, Achyranthis Radix, and Glycyrrhizae Radix was obtained in comparison with the weight of raw herbs. The extract was prepared to be in a weight ratio of 1:1.5:1.5.

Comparative Example 7

Preparation of Extract of Cibotii Rhizoma, Ledebouriellae Radix, Achyranthis Radix, Acgtrabtgus budebtatae Radix and Eucommiae cortex By the same extraction method in <Example 1>, 9.94% of extract of Cibotii Rhizoma, Ledebouriellae Radix, Achyranthis Radix, Acgtrabtgus budebtatae Radix and Eucommiae cortex was obtained in comparison with the weight of raw herbs. The extract was prepared to be in a weight ratio of 1:1.5:1.5:1.5.

Experimental Example 1

Examination of Anti-Inflammatory Effect of Extract of Cibotii Rhizoma, Ledebouriellae Radix, Achyranthis Radix, *Paeonia lactiflora* Pall, and Glycyrrhizae Radix <1-1> Measurement of Effect of Extract of Cibotii Rhizome, Ledebouriellae Radix, Achyranthis Radix, *Paeonia lactiflora* Pall, and Glycyrrhizae Radix on Cell Survival Rate To examine the effects of the extract of Cibotii Rhizoma, Ledebouriellae Radix, Achyranthis Radix, *Paeonia lactiflora* Pall, and Glycyrrhizae Radix prepared by the method described in <Example 1> and extracts prepared by the methods described in <Comparative Example 1>, <Comparative Example 2>, <Comparative Example 3>, <Comparative Example 4>, <Comparative Example 5>, <Comparative Example 6>, and <Comparative Example 7> on the cell survival rate, the following method was performed.

Specifically, Raw 264.7 macrophages were purchased from Korean Cell Line Bank, and the cells were cultured using DMEM medium containing 10% FBS, 100 ug/ml penicillin and streptomycin antibiotics in a 37° C., 5% $CO_2$ incubator. Then, Raw 264.7 cells were dispensed at a concentration of $5 \times 10^6$ cells into a 96-well plate, and cultured in a 37° C., 5% $CO_2$ incubator for 24 hours. Different concentrations of 100, 200, 400, or 800 ug/ml of the extract of Cibotii Rhizoma, Ledebouriellae Radix, Achyranthis Radix, *Paeonia lactiflora* Pall, and Glycyrrhizae Radix prepared by the method described in <Example 1> and extracts prepared by the methods described in <Comparative Example 1>, <Comparative Example 2>, <Comparative Example 3>, <Comparative Example 4>, <Comparative Example 5>, <Comparative Example 6>, and <Comparative Example 7> were treated to cultured cells, and cells were incubated for 24 hours. Then, the medium was removed from the culture fluid, 5 mg/ml per well of MTT (3-(4,5-dimethylthiazol-2-yl)-2,5-diphenyltetrazolium bromide) reagent was added to the cells, and cells were incubated at 37° C. for 3 hours and then, the medium was removed. To dissolve formazan attached to the bottom of the well, 200 ul of DMSO was treated. Then, the well was agitated with a vortex mixer for an additional 10 minutes, and absorption was measured at 650 nm wavelength using a microplate reader. To compare cytotoxicity, Raw 264.7 cells to which any material was not treated were used as a reference control, and for a negative control, LPS was treated to Raw 264.7 cells and the same method as above was performed to confirm the cell survival rate.

Consequently, as shown in Table 1 and FIG. 1, it was found that when the cell survival rate was compared between the treatment group in which different concentration of the extract of Cibotii Rhizoma, Ledebouriellae Radix, Achyranthis Radix, *Paeonia lactiflora* Pall, and Glycyrrhizae Radix prepared by the method described in <Example 1> was treated to Raw 264.7 cells and the treatment groups in which extracts prepared by the methods described in <Comparative Example 1>, <Comparative Example 2>, <Comparative Example 3>, <Comparative Example 4>, <Comparative Example 5>, <Comparative Example 6>, and <Comparative Example 7> were treated to the cells, the cell survival rate of the treatment group in which the extract of Cibotii Rhizoma, Ledebouriellae Radix, Achyranthis Radix, *Paeonia lactiflora* Pall, and Glycyrrhizae Radix was treated was higher (see Table 1 and FIG. 1).

TABLE 1

| Treatment Group | 800 ug/ml | 400 ug/ml | 200 ug/ml | 100 ug/ml |
|---|---|---|---|---|
| cells only | 100.0000 | 100.0000 | 100.0000 | 100.0000 |
| LPS only | 75.8973 | 75.8973 | 75.8973 | 75.8973 |
| Cibotii Rhizoma + Ledebouriellae Radix + Achyranthis Radix (Comparative example 1) | 90.3782 | 90.4749 | 87.3136 | 95.0304 |
| Paeonia lactiflora Pall (Comparative example 2) | 90.3368 | 90.9304 | 86.0712 | 90.3782 |
| Glycyrrhizae Radix (Comparative example 3) | 91.7587 | 86.2921 | 93.1115 | 90.9304 |
| Paeonia lactiflora Pall + Glycyrrhizae Radix (Comparative example 4) | 91.9105 | 90.9304 | 87.3136 | 88.7907 |

TABLE 1-continued

| Treatment Group | 800 ug/ml | 400 ug/ml | 200 ug/ml | 100 ug/ml |
|---|---|---|---|---|
| Cibotii Rhizoma + Ledebouriellae Radix + Achyranthis Radix + Paeonia lactiflora Pall (Comparative example 5) | 90.8614 | 88.5008 | 90.5301 | 87.3136 |
| Cibotii Rhizoma + Ledebouriellae Radix + Achyranthis Radix + Glycyrrhizae Radix (Comparative example 6) | 90.3782 | 89.8951 | 90.0469 | 91.9105 |
| Cibotii Rhizoma + Ledebouriellae Radix + Achyranthis Radix + Paeonia lactiflora Pall + Glycyrrhizae Radix (Example 1) | 90.8890 | 90.9028 | 90.3782 | 91.5516 |
| Cibotii Rhizoma + Ledebouriellae Radix + Achyranthis Radix + Acgtrabtgus budebtatae Radix + Eucommiae cortex (Comparative example 7) | 88.7907 | 89.3291 | 88.8045 | 91.0823 |

<1-2> Examination of Effect of Extract of Cibotii Rhizoma, Ledebouriellae Radix, Achyranthis Radix, *Paeonia lactiflora* Pall, and Glycyrrhizae Radix on Nitric Oxide (NO) Production Nitric Oxide was induced by treating RAW 264.7 cells with LPS (lipopolysaccharide), and then, the extract of Cibotii Rhizoma, Ledebouriellae Radix, Achyranthis Radix, *Paeonia lactiflora* Pall, and Glycyrrhizae Radix prepared by the method described in <Example 1> and extracts prepared by the methods described in <Comparative Example 1>, <Comparative Example 2>, <Comparative Example 3>, <Comparative Example 4>, <Comparative Example 5>, <Comparative Example 6>, and <Comparative Example 7> were treated to the cells, and in order to examine change in NO production, the following method was performed.

Specifically, RAW 264.7 cells were dispensed at a concentration of $5 \times 10^6$ cells into a 96-well plate and cultured by the method described in <Example 1>. Then, 1 ug/ml concentration of LPS (lipopolysaccharide) was treated to each well, and different concentrations of 100, 200, 400, or 800 ug/ml of the extract of Cibotii Rhizoma, Ledebouriellae Radix, Achyranthis Radix, *Paeonia lactiflora* Pall, and Glycyrrhizae Radix prepared by the method described in <Example 1> and extracts prepared by the methods described in <Comparative Example 1>, <Comparative Example 2>, <Comparative Example 3>, <Comparative Example 4>, <Comparative Example 5>, <Comparative Example 6>, and <Comparative Example 7> were treated to the cells, and the cells were cultured for 20 hours. To 100 ug of the supernatant of the cultured cells, 180 ul of Griess reagent was treated and mixed. After 20 minutes, nitric oxide (NO) was measured at 540 nm wavelength using a microplate reader. To compare NO production, Raw 264.7 cells to which any material was not treated were used as a reference control, and for a negative control, LPS was treated to Raw 264.7 cells and the same method as above was performed to measure NO concentration.

Consequently, as shown in Table 2 and FIG. 2, it was found that when the NO production was compared between the treatment group in which the extract of Cibotii Rhizoma, Ledebouriellae Radix, Achyranthis Radix, *Paeonia lactiflora* Pall, and Glycyrrhizae Radix prepared by the method described in <Example 1> was treated to the cells and the treatment groups in which extracts prepared by the methods described in <Comparative Example 1> to <Comparative Example 7> were treated to the cells, the NO production of the treatment group in which the extract of Cibotii Rhizoma, Ledebouriellae Radix, Achyranthis Radix, *Paeonia lactiflora* Pall, and Glycyrrhizae Radix was treated decreased effectively (see Table 2 and FIG. 2).

Accordingly, from the results of <Experimental Example 1> and <Experimental Example 2>, it was found that the extract of Cibotii Rhizoma, Ledebouriellae Radix, Achyranthis Radix, *Paeonia lactiflora* Pall, and Glycyrrhizae Radix was superior to the extracts of <Comparative Example 1>, <Comparative Example 2>, <Comparative Example 3>, <Comparative Example 4>, <Comparative Example 5>, <Comparative Example 6>, and <Comparative Example 7>.

TABLE 2

| Treatment Group | 800 ug/ml | 400 ug/ml | 200 ug/ml | 100 ug/ml |
|---|---|---|---|---|
| cells only | 2.4511 | 2.4511 | 2.4511 | 2.4511 |
| LPS only | 48.8591 | 48.8591 | 48.8591 | 48.8591 |
| Comparative example 1 | 25.5636 | 34.0182 | 34.4727 | 35.8364 |
| Comparative example 2 | 26.6545 | 28.3870 | 30.4727 | 33.0182 |
| Comparative example 3 | 23.3818 | 32.8364 | 38.2442 | 43.1091 |
| Comparative example 4 | 23.4727 | 28.0182 | 35.5632 | 40.9273 |
| Comparative example 5 | 23.3818 | 30.2909 | 40.7455 | 47.0182 |
| Comparative example 6 | 23.0182 | 33.2909 | 33.7455 | 43.1091 |
| Example 1 | 9.4457 | 11.2659 | 20.4480 | 21.3557 |
| Comparative example 7 | 13.4546 | 17.5659 | 25.1359 | 26.5468 |

Experimental Example 2

In Vitro Examination of Protein Expression-Inhibitory Effect of Extract of Cibotii Rhizoma, Ledebouriellae Radix, Achyranthis Radix, *Paeonia lactiflora* Pall, and Glycyrrhizae Radix <2-1> Cell Culture To articular synovial cells separated from patients of rheumatoid arthritis who visited Jaseng Hospital of Korean Medicine (Seoul, Republic of Korea, 5% DMEM (Dulbecco's modified Eagle's medium) containing penicillin/streptomycin was added. The cells were dispensed at a concentration of $1 \times 10^4$ cells into a 6-well culture dish, and cultured at 37° C. for 24 hours.

<2-2> Examination of COX-2 Protein Expression Inhibition by Extract of Cibotii Rhizoma, Ledebouriellae Radix, Achyranthis Radix, *Paeonia lactiflora* Pall, and Glycyrrhizae Radix In order to examine whether the extract of Cibotii Rhizoma, Ledebouriellae Radix, Achyranthis Radix, *Paeonia lactiflora* Pall, and Glycyrrhizae Radix of the present invention has an effect on osteoarthritis or not, the following method was performed to examine the effect on the expression of inflammatory cytokine, COX-2 protein, which is a marker for osteoarthritis.

Specifically, cells cultured by the same method as in Experimental Example <2-1> were dispensed at a concentration of $1 \times 10^5$ cells into a 75 flask, and cultured for 7 days. To the cultured cells, 50 ng/ml of LPS was added, and stimulation was applied for 2 hours. Then, the extract of Cibotii Rhizoma, Ledebouriellae Radix, Achyranthis Radix, *Paeonia lactiflora* Pall, and Glycyrrhizae Radix prepared by the method described in <Example 1> and extracts prepared by the same methods in <Comparative Example 1>, <Comparative Example 2>, <Comparative Example 3>, <Comparative Example 4>, <Comparative Example 5>, <Comparative Example 6>, and <Comparative Example 7> were added to be a final concentration of 50 ug/ml to the cells. The cells were transferred to a 1.5 ml eppendorf tube, centrifuged at 15,000 rpm for 5 minutes to remove the supernatant. 200 ul of RNA zol solution was added to the tube, and then, 50 ul of chloroform was added, and pipetted. The cells were lysed, centrifuged at 15,000 rpm at 4° C. for 15 minutes to obtain total RNA, and isopropanol was added thereto, and precipitated at 4° C. for 15 minutes. Then, the cells were washed using 75% ethanol, dried, and 20 ul of RNase free $dH_2O$ was added thereto, and the cells were lysed at 60° C. for 30 minutes. 5 ul of 10 mM dNTP, 26 ul of 25 mM $MgCl$, 5 ul of 10×RNA PCR buffer, 1 ul of RNase inhibitor, 1 ul of AMV-Optimized Taq, 1 ul of AMV reverse transcriptase, 1 ul of each forward/reverse 50 pM specific primer (Table 3), and 26 ul of RNase-free $dH_2O$ were added to 5 ul of the lysed total RNA. Reverse transcription reaction was performed at 50° C. for 20 minutes, and the reaction was stopped at 94° C. for 2 minutes to perform DNA synthesis reaction (polymerase chain reaction: PCR). The condition for DNA synthesis reaction (polymerase chain reaction: PCR) was as follows: 35 cycles of 94° C. for 1 minute, 55° C. for 45 seconds, and 70° C. for 60 seconds, and final elongation reaction at 70° C. for 5 minutes. Electrophoresis was performed on 1% agarose gel, and band intensity was quantified using Scion-Image (Scion Corporation, Maryland, USA) for Window Program. Experimental results were expressed as mean±S.D. One-way analysis of variance was carried out using Sigma Stat (Jandel Co.; San Rafael, Calif., USA). Differences at *P<0.05 and **P<0.01 were considered statistically significant.

Consequently, as shown in FIG. 3, the present inventors treated the extract of Cibotii Rhizoma, Ledebouriellae Radix, Achyranthis Radix, *Paeonia lactiflora* Pall, and Glycyrrhizae Radix prepared by the method described in <Example 1> to articular synovial cells in which inflammation was induced by LPS and examined the expression of COX-2, and found that the expression of COX-2 was inhibited effectively compared to the cells in which extracts in <Comparative Example 1> to <Comparative Example 7> were treated (FIG. 3).

TABLE 3

| Sequence Number | Sequence Number |
|---|---|
| SEQ NO: 1 (COX 2_F) | 5'-GCT GGC CTG GTA CTC AGT AGG TT-3' |
| SEQ NO: 2 (COX 2_R) | 5'-CGA GGC CAC TGA TAC CTA TTG C-3' |

<2-3> Examination of iNOS Expression Inhibition by Extract of Cibotii Rhizoma, Ledebouriellae Radix, Achyranthis Radix, *Paeonia lactiflora* Pall, and Glycyrrhizae Radix In order to examine whether the extract of Cibotii Rhizoma, Ledebouriellae Radix, Achyranthis Radix, *Paeonia lactiflora* Pall, and Glycyrrhizae Radix of the present invention has an effect on osteoarthritis or not, the following method was performed to examine the effect on the expression of inducible nitric oxide synthetase (iNOS), which is a marker for osteoarthritis.

Specifically, cells cultured by the same method as in Experimental Example <2-1> were dispensed at a concentration of $1 \times 10^5$ cells into a 75 flask, and cultured for 7 days. To the cultured cells, 50 ng/ml of LPS was added, and stimulation was applied for 2 hours. Then, the extract of Cibotii Rhizoma, Ledebouriellae Radix, Achyranthis Radix, *Paeonia lactiflora* Pall, and Glycyrrhizae Radix prepared by the method described in <Example 1> and extracts prepared by the same methods in <Comparative Example 1>, <Comparative Example 2>, <Comparative Example 3>, <Comparative Example 4>, <Comparative Example 5>, <Comparative Example 6>, and <Comparative Example 7> were added to be a final concentration of 50 ug/ml to the cells. The cells were transferred to a 1.5 ml eppendorf tube, centrifuged at 15,000 rpm for 5 minutes to remove the supernatant. 200 ul of RNA zol solution was added to the tube, and then, 50 ul of chloroform was added, and pipetted. The cells were lysed, centrifuged at 15,000 rpm at 4° C. for 15 minutes to obtain total RNA, and isopropanol was added thereto, and precipitated at 4° C. for 15 minutes. Then, the cells were washed using 75% ethanol, dried, and 20 ul of RNase free $dH_2O$ was added thereto, and the cells were lysed at 60° C. for 30 minutes. 5 ul of 10 mM dNTP, 26 ul of 25 mM $MgCl$, 5 ul of 10×RNA PCR buffer, 1 ul of RNase inhibitor, 1 ul of AMV-Optimized Taq, 1 ul of AMV reverse transcriptase XL, 1 ul of each forward/reverse 50 pM specific primer (Table 4), and 26 ul of RNase-free $dH_2O$ were added to 5 ul of the lysed total RNA. Reverse transcription reaction was performed at 50° C. for 20 minutes, and the reaction was stopped at 94° C. for 2 minutes to perform DNA synthesis reaction (polymerase chain reaction: PCR). The condition for DNA synthesis reaction (polymerase chain reaction: PCR) was as follows: 35 cycles of 94° C. for 1 minute, 55° C. for 45 seconds, and 70° C. for 60 seconds, and final elongation reaction at 70° C. for 5 minutes. Electrophoresis was performed on 1% agarose gel. Experimental results were expressed as mean±S.D. One-way analysis of variance was carried out using Sigma Stat (Jandel Co.; San Rafael, Calif., USA). Differences at *P<0.05 and **P<0.01 were considered statistically significant.

Consequently, as shown in FIG. 4, the present inventors treated the extract of Cibotii Rhizoma, Ledebouriellae Radix, Achyranthis Radix, *Paeonia lactiflora* Pall, and Glycyrrhizae Radix prepared by the method described in <Example 1> to articular synovial cells in which inflammation was induced by LPS and examined the expression of iNOS, and found that the expression of iNOS was inhibited effectively compared to the cells in which extracts in <Comparative Example 1> to <Comparative Example 7> were treated (FIG. 4).

TABLE 4

| Sequence Number | Sequence |
|---|---|
| SEQ NO: 3 iNOS_F | CCTGGAGGTTCTGGATGAGA |
| SEQ NO: 4 iNOS_R | GTAGTAGCGGGGCTTCAAGA |

<2-4> Examination of MMP Expression Inhibition by Extract of Cibotii Rhizome, Ledebouriellae Radix, Achyranthis Radix, *Paeonia lactiflora* Pall, and Glycyrrhizae Radix When cartilage tissue is destroyed, MMPs are generally activated and the expression increases. MMPs are a proteolytic enzyme which destroys matrix components in bone and cartilage, and it has been reported that MMPs play a major role in processes such as differentiation of normal tissues, wound healing, organ formation, reproduction, angiogenesis, tissue absorption and remodeling, etc., and are expressed also in a pathological condition such as arthritis, and play a major role in etiology (Patwari P et al., 2003). Accordingly, the following method was performed to examine the effect of the extract of Cibotii Rhizoma, Ledebouriellae Radix, Achyranthis Radix, *Paeonia lactiflora* Pall, and Glycyrrhizae Radix on MMP expression.

Specifically, in order to examine the effect of the extract of Cibotii Rhizoma, Ledebouriellae Radix, Achyranthis Radix, *Paeonia lactiflora* Pall, and Glycyrrhizae Radix prepared by the same method in <Example 1>, cells cultured by the same method in Experimental Example <2-1> were dispensed at a concentration of $5 \times 10^6$ cells into DMEM medium containing 10% FBS in a 6-well plate, and stabilized for 12 hours. The extract of Cibotii Rhizoma, Ledebouriellae Radix, Achyranthis Radix, *Paeonia lactiflora* Pall, and Glycyrrhizae Radix prepared by the method described in <Example 1>, extracts prepared by the methods described in <Comparative Example 1>, <Comparative Example 2>, <Comparative Example 3>, <Comparative Example 4>, <Comparative Example 5>, <Comparative Example 6>, and <Comparative Example 7> were treated along with $H_2O_2$ to articular synovial cells for 2 hours, and cells were collected using 0.25% trypsin-EDTA, and total RNA was extracted using RNeasy extraction kit (QIAGEN, Valencia, Calif., USA) according to the manufacturer's protocol. For cDNA synthesis, each of 4 μL of 5× iScript select reaction mix, 2 μL of oligo(dT) primer set (Table 1), 5 μL of RNA sample, 8 μL of nuclease-free water was added to 5 μg of total RNA, and 1 μL of iScript Reverse Transcriptase was added thereto at the end, followed by mixing up and down evenly with a pippet. After performing the reaction at 42° C. for 60 minutes, and at 82° C. for 5 minutes, synthesized cDNA was used for PCR. The machine used for the real-time PCR experiment was Step One Real-Time PCR system (Applied Biosystems, Foster City, Calif., USA) and PCR was performed according to the protocol of iQ SYBR Green Supermix (BIO-RAD). The final concentration of the mixed solution for PCR was 2 μL of cDNA (10 to 100 ng), 10 μL of 2× iQ SYBR Green Supermix, 1 μL of each forward & reverse primer (250 nM), and 7 μL of $H_2O$. PCR analysis was performed as follows: hot start at 95° C. for 10 minutes; 40 cycles of 95° C. for 15 seconds, 55° C. for 15 seconds, and 75° C. for 30 seconds; and a polishing step at 95° C. for 15 seconds. Primers used for the reaction was as described in the following [Table 5]. Experimental results were expressed as mean±S.D. One-way analysis of variance was carried out using Sigma Stat (Jandel Co.; San Rafael, Calif., USA). Differences at *P<0.05 and **P<0.01 were considered statistically significant.

Consequently, as shown in FIG. 5, the present inventors treated the extract of Cibotii Rhizoma, Ledebouriellae Radix, Achyranthis Radix, *Paeonia lactiflora* Pall, and Glycyrrhizae Radix prepared by the method described in <Example 1> to articular synovial cells in which inflammation was induced by LPS treatment and examined the expression of MMP-13, and found that the expression of MMP-13 was reduced effectively compared to the cells in which extracts in <Comparative Example 1> to <Comparative Example 7> were treated (FIG. 5).

TABLE 5

| Sequence Number | Sequence |
| --- | --- |
| SEQ NO: 5 MMP-13_F | ACG TTC AAG GAA TCC AGT CTC TCT |

TABLE 5 -continued

| Sequence Number | Sequence |
| --- | --- |
| SEQ NO: 6 MMP-13_R | GGA TAG GGC TGG GTC ACA CTT |
| SEQ NO: 7 GAPDH_F | TGG CCT CCA AGG AGT AAG AAA C |
| SEQ NO: 8 GAPDH_R | CAG CAA CTG AGG GCC TCT CT |

Experimental Example 3

Examination of In Vivo Pain-Inhibitory Effect of Extract of Cibotii Rhizoma, Ledebouriellae Radix, Achyranthis Radix, *Paeonia lactiflora* Pall, and Glycyrrhizae Radix <3-1> Experimental Animal Rearing Animals used in the present invention were 7 to 8 weeks old white rats (Spraque-Dawley, 185 to 250 g, male), and the animals were purchased from Jeil trade corporation (Republic of Korea). Rats were fed with normal diet and accommodated for 1 week to perform the experiment. Under a 12 hour light/dark cycle, rats had free access to food and water, and bred and maintained under PF (pathogen free) environment at 23±1° C. with relative humidity of 56%.

<3-2> Examination of Pain-Inhibitory Effect of Extract of Cibotii Rhizome, Ledebouriellae Radix, Achyranthis Radix, *Paeonia lactiflora* Pall, and Glycyrrhizae Radix To examine the pain-inhibitory effect of the extract of Cibotii Rhizoma, Ledebouriellae Radix, Achyranthis Radix, *Paeonia lactiflora* Pall, and Glycyrrhizae Radix of the present invention, the following method was performed.

Specifically, the extract of Cibotii Rhizoma, Ledebouriellae Radix, Achyranthis Radix, *Paeonia lactiflora* Pall, and Glycyrrhizae Radix prepared by the same method in <Example 1> and extracts prepared by the methods described in <Comparative Example 1> to <Comparative Example 7> were dissolved in physiological saline (1 ml/100 g b.wt.) at a dose of 100 and 300 mg/kg body weight, and were orally administered using a sonde needle. Administration volume was calculated from the bodyweight measured on the day of administration. Control rats were administered only with physiological saline (1 ml/100 g b.wt.). For a positive control group, phenylbutazone was suspended into 0.5% methylcellulose solution at a dose of 50 mg/kg/5 ml to administer orally. After 30 minutes of administration, 0.7% acetic acid-saline (0.1 mg/10 g b.wt.) was injected intraperitoneally, the number of pains (writhing) was measured between 5 to 10 minutes after the injection (Koster et al., 1959). Statistical significance test for each experimental group was performed as follows. Levene's test was performed to examine variance homogeneity of data obtained from each experimental group. If the data showed variance homogeneity, one-was ANOVA was performed, and if the test result was considered to be significant at a level of p=0.05, difference between experimental groups were compared by Dunnett's test (Process 1). If the data showed variance heterogeneity, data transformation was performed, and Levene's test was performed again on the transformed data. If the data showed variance homogeneity, verification was performed according to Process 1. However, if the data showed variance heterogeneity, non-parametric ANOVA test was performed. If the result was significant, statistical significance was verified by Wilcoxon-Mann-Whitney rank sum test (Process 2).

Consequently, as shown in Table 6, it was found that the number of pains (writhing) measured in the group in which the extract of Cibotii Rhizoma, Ledebouriellae Radix, Achyranthis Radix, *Paeonia lactiflora* Pall, and Glycyrrhizae Radix in <Example 1> was administered was smaller than those in the groups in which extracts of <Comparative Example 1> to <Comparative Example 7> were administered, and that the number of pains (writhing) measured in the group in which the extract of the present invention was administered was similar to the positive control group in which phenylbutazone was administered.

Accordingly, from the result of Experimental Example <3-2>, it was proved that the extract of the present invention had similar pain-inhibitory effect to phenylbutazone (Table 6).

TABLE 6

| Group | Administration dose (mg/kg) | Number of writhing | Inhibition rate (%) |
|---|---|---|---|
| Control | 0 | 24.7 ± 2.0 | |
| Example 1 | 100 | 12.1 ± 3.6 | 50.9 |
| | 300 | 13.3 ± 1.8 | 46.4 |
| Comparative example 1 | 100 | 13.3 ± 1.8 | 46.2 |
| | 300 | 9.6 ± 1.8 | 61.2 |
| Comparative example 2 | 100 | 11.0 ± 1.5 | 52.2 |
| | 300 | 11.6 ± 1.5 | 53.2 |
| Comparative example 3 | 100 | 9.6 ± 1.8 | 61.2 |
| | 300 | 13.3 ± 1.8 | 46.4 |
| Comparative example 4 | 100 | 11.6 ± 1.5 | 53.2 |
| | 300 | 11.3 ± 1.5 | 52.7 |
| Comparative example 5 | 100 | 13.3 ± 1.8 | 46.4 |
| | 300 | 9.6 ± 1.8 | 61.2 |
| Comparative example 6 | 100 | 9.6 ± 1.8 | 61.2 |
| | 300 | 11.6 ± 1.5 | 55.2 |
| Comparative example 7 | 100 | 11.2 ± 2.5 | 54.6 |
| | 300 | 14.3 ± 2.3 | 44.3 |
| Positive control (Phenylbutazone) | 50 | 12.2 ± 0.8 | 50.1 |

Experimental Example 4

Examination of In Vivo Arthritis Edema-Inhibitory Effect of Extract of Cibotii Rhizoma, Ledebouriellae Radix, Achyranthis Radix, *Paeonia lactiflora* Pall, and Glycyrrhizae Radix <4-1> Experimental Animal Rearing Animals used in the present invention were white rats reared by the method described in Experimental Example <3-1>.

<4-2> Examination of Arthritis Edema-Inhibitory Effect of Extract of Cibotii Rhizoma, Ledebouriellae Radix, Achyranthis Radix, *Paeonia lactiflora* Pall, and Glycyrrhizae Radix To examine arthritis edema-inhibitory effect by administering to white rats reared by the method described in Experimental Example <3-1> the extract of Cibotii Rhizoma, Ledebouriellae Radix, Achyranthis Radix, *Paeonia lactiflora* Pall, and Glycyrrhizae Radix prepared by the same method in <Example 1>, the following method was performed.

Specifically, 6 animals per experimental group of white rat (200 g) reared by the method described in Experimental Example <3-1> were selected, and to induce arthritis edema, 0.5 ml of ZYMOSAN-A (20 mg/ml/KG) and 0.5 ml of Freund's adjuvant were mixed and administered to left Zusanli of white rats. The volume of foot was measured using an edema measuring instrument, plethysmometer (Ugo Basile, Italy) and was compared to the volume of foot before administration of the extract of <Example 1> to calculate the edema increase rate (Mathematical formula 1). To edema-induced white rats, the extract of Cibotii Rhizoma, Ledebouriellae Radix, Achyranthis Radix, *Paeonia lactiflora* Pall, and Glycyrrhizae Radix prepared by the same method in <Example 1> and extracts prepared by the same methods in <Comparative Example 1> to <Comparative Example 7> were orally administered at 1 ml/1 kg of body weight once a day, repeatedly for 14 days. To compare the edema increase rate between rats administered with different extracts, the edema increase rate was calculated (Mathematical formula 2).

Edema increase rate(%)=(foot edema after administration of inflammation inducer−foot edema before administration of inflammation inducer)/foot edema before administration of inflammation inducer×100     [Mathematical formula 1]

Edema inhibition rate(%)=(mean edema rate of the control group−mean edema rate of the drug administration group)/mean edema rate of the control group×100     [Mathematical formula 2]

Consequently, as shown in Table 7, it was found that edema was induced since $4^{th}$ day in arthritis edema-induced rats. When comparing the Zusanli edema between rats administered with the extract of Cibotii Rhizoma, Ledebouriellae Radix, Achyranthis Radix, *Paeonia lactiflora* Pall, and Glycyrrhizae Radix and rats administered with extracts of <Comparative Example 1> to <Comparative Example 7>, it was found that the edema in rats administered with the extract of the present invention was remarkably reduced (Table 7).

TABLE 7

| Extract | Edema Inhibition rate (%) |
|---|---|
| Control | — |
| Example 1 | 9.5 |
| Comparative example 2 | 17.5 |
| Comparative example 3 | 16.3 |
| Comparative example 4 | 18.9 |
| Comparative example 5 | 17.8 |
| Comparative example 6 | 16.5 |
| Comparative example 7 | 16.3 |
| Comparative example 8 | 17.2 |

Experimental Example 5

Examination of Nerve Cell Regenerative Effect of Extract of Cibotii Rhizoma, Ledebouriellae Radix, Achyranthis Radix, *Paeonia lactiflora* Pall, and Glycyrrhizae Radix <5-1> Cell Culture PC12 cells (KCLB 21721, Korean Cell Line Bank, Seoul, Korea) which have characteristics of nerve cells and were induced from rat pheochromocytoma were used. PC12 cells were inoculated to RPMI 1640 medium including 25 mM HEPES, 25 mM sodium bicarbonate, 10% fetal bovine serum, 50 units/mL penicillin and 100 mg/mL streptomycin to culture in an incubator under a condition of 37° C., 5% $CO_2$.

<5-2> Examination of Nerve Cell Protective Effect of Extract of Cibotii Rhizoma, Ledebouriellae Radix, Achyranthis Radix, *Paeonia lactiflora* Pall, and Glycyrrhizae Radix To examine whether the extract of Cibotii Rhizoma, Ledebouriellae Radix, Achyranthis Radix, *Paeonia lactiflora* Pall, and Glycyrrhizae Radix of the present invention has nerve cell protective effect or not, the following method was performed.

Specifically, to PC12 cells cultured by the method described in Experimental Example <4-1>, the extract of Cibotii Rhizoma, Ledebouriellae Radix, Achyranthis Radix, *Paeonia lactiflora* Pall, and Glycyrrhizae Radix prepared by the same method in <Example 1> and extracts prepared by the same methods in <Comparative Example 1> to <Comparative Example 7> were treated, and the cell survival rate was measured. After pre-incubation of PC12 cells with the above extract for 48 hours, incubation with 200 μM $H_2O_2$ for 3 hours and incubation with MTT at 37° C. for 3 hours were performed in order, and 100 μL of DMSO was added to stop the reaction. Absorption was measured at 570 nm (determination) and 690 nm (reference wave) using a microplate reader (680, Bio-rad, Tokyo, Japan). PC12 cells were pre-incubated with different concentrations of extracts for 48 hours, and then treated with 200 μM $H_2O_2$, and incubated for 3 hours. Centrifugation at 250×g for 5 minutes was performed to precipitate, and 100 μL of the supernatant was transferred to a new well, and the PC12 cellular membrane damage protective effect was measured by LDH assay kit (Sigma-Aldrich Chemical Co.).

Consequently, as shown in FIG. 6, it was found that the cell survival rate of the PC12 cells to which the extract of Cibotii Rhizoma, Ledebouriellae Radix, Achyranthis Radix, *Paeonia lactiflora* Pall, and Glycyrrhizae Radix prepared by the method described in <Example 1> was treated was higher than that of the PC12 cells to which extracts prepared by the same method in <Comparative Example 1> to <Comparative Example 7> were treated (FIG. 6).

Also, as shown in FIG. 7, when PC12 cells were treated with $H_2O_2$ only, it was found that cell membrane was considerably damaged as LDH release increased. When comparing LDH release between cell membranes in which the extract of Cibotii Rhizoma, Ledebouriellae Radix, Achyranthis Radix, *Paeonia lactiflora* Pall, and Glycyrrhizae Radix of <Example 1> was treated and cell membranes in which extracts prepared by the same method in <Comparative Example 1> to <Comparative Example 7> were treated, it was found that LDH release in cell membranes in which the extract of <Example 1> was treated was remarkably reduced (FIG. 7). Accordingly, from the result of Experimental Example <4-2>, it was confirmed that the extract of Cibotii Rhizoma, Ledebouriellae Radix, Achyranthis Radix, *Paeonia lactiflora* Pall, and Glycyrrhizae Radix of the present invention had nerve cell protective effect.

Experimental Example 6

Examination of Clinical Pharmacological Effect of Cibotii Rhizoma, Ledebouriellae Radix, Achyranthis Radix, *Paeonia lactiflora* Pall, and Glycyrrhizae Radix <6-1> Recruitment of Subjects Among Koreans, a group of patients (5 patients) who were identified having disc diseases and being treated were recruited from Jaseng Hospital of Korean Medicine (Seoul, Republic of Korea), and those patients were identified within one month of the occurrence of disc disease by Jaseng Hospital of Korean Medicine. Informed consent was obtained from every participant via Jaseng Medical Foundation Spine and Joint Research Institute (JSR), and this research was approved by JSR research ethics committee.

<6-2> Examination of Effect of Cibotii Rhizoma, Ledebouriellae Radix, Achyranthis Radix, *Paeonia lactiflora* Pall, and Glycyrrhizae Radix on Disc Patients To examine clinical pharmacological effects by administering to disc patients recruited by the method described in Experimental Example <6-1> the extract of Cibotii Rhizoma, Ledebouriellae Radix, Achyranthis Radix, *Paeonia lactiflora* Pall, and Glycyrrhizae Radix prepared by the method described in <Example 1>, the following method was performed.

Specifically, MRI was performed to classify the detailed etiology of disc patients (5 patients) recruited by the method described in Experimental Example <6-1>. As shown in the following [Table 8], different disc symptoms were found from all five patients (Table 8). Then, the extract of Cibotii Rhizoma, Ledebouriellae Radix, Achyranthis Radix, *Paeonia lactiflora* Pall, and Glycyrrhizae Radix prepared by the method described in <Example 1> was administered to disc patients twice, 975.32 mg dose each, for 6 months. MRI was performed to examine the effect of the extract of Cibotii Rhizoma, Ledebouriellae Radix, Achyranthis Radix, *Paeonia lactiflora* Pall, and Glycyrrhizae Radix on disc patients.

Figure 12:
FIG. 12 shows a result of the MRI scan of patient 5 with disc disease taken the mixed extract of Cibotii Rhizoma, Ledebouriellae Radix, Achyranthis Radix, *Paeonia lactiflora* Pall, and Glycyrrhizae Radix for 6 months.

Consequently, as shown in FIG. 8 to FIG. 12, the extract of Cibotii Rhizoma, Ledebouriellae Radix, Achyranthis Radix, *Paeonia lactiflora* Pall, and Glycyrrhizae Radix prepared by the method described in <Example 1> was administered to disc patients having different disc etiology for 6 months and MRI was taken. Decrease in extruded disc volume and improvement in the degree of neuromembrane and nerve-root compression were observed in disc patient 1 (FIG. 8), absorption of extruded disc and decrease in extruded disc volume were observed in disc patient 2 (FIG. 9), decrease in volume and absorption were observed in disc patient 3 and disc patient 4 (FIG. 10 and FIG. 11), and decrease in sequestered disc volume and absorption of the sequestered disc were observed in disc patient 5 (FIG. 12).

Accordingly, from the result of <Experimental Example 7>, it was found that the extract of Cibotii Rhizoma, Ledebouriellae Radix, Achyranthis Radix, *Paeonia lactiflora* Pall, and Glycyrrhizae Radix could decrease and absorb disc volume effectively.

TABLE 8

| Disc patient (number) | Disc etiology |
|---|---|
| Disc patient 1 | Disc which compresses neuromembrane and nerve-root is observed. |
| Disc patient 2 | Downward transition of extruded disc at L3/L4 is observed. |
| Disc patient 3 | Protruded disc and sequestered disc is observed at L4/L5. |
| Disc patient 4 | Upward transition of extruded disc at L4/L5 is observed. |
| Disc patient 5 | Sequestered disc is observed at L5/S1. |

Preparation Example 1

Preparation of Pharmaceutical Formulations

<1-1> Powder Preparation 2 g of the mixed extract of the present invention
1 g of lactose The above ingredients are mixed, and filled into an airtight bag to prepare a powder.

<1-2> Tablet Preparation 100 mg of the mixed extract of the present invention
100 mg of corn starch
100 mg of lactose
2 mg of magnesium stearate The above ingredients are mixed, and tabletted according to a conventional tablet preparation method to prepare a tablet.

<1-3> Capsule Preparation 100 mg of the mixed extract of the present invention
100 mg of corn starch
100 mg of lactose
2 mg of magnesium stearate The above ingredients are mixed, and filled in a gelatin capsule according to a conventional capsule preparation method to prepare a capsule.

<1-4> Pill Preparation 1 g of the mixed extract of the present invention
1.5 g of lactose
1 g of glycerin
0.5 g of xylitol The above ingredients are mixed to prepare a pill (4 g per pill) according to a conventional method.

<1-5> Granule Preparation 150 mg of the mixed extract of the present invention
50 mg of soybean extracts
200 mg of glucose
600 mg of starch The above ingredients are mixed, 100 mg of 30% ethanol is added thereto, and the mixture is dried at 60° C. to form granules, and then filled into a bag.

Preparation Example 2

Preparation of Health Foods

<2-1> Preparation of Wheat Flour Foods 0.5-5.0 parts by weight of the mixed extract of the present invention were added to wheat flour, and bread, cakes, cookies, crackers, and noodles were prepared using this mixture.

<2-2> Preparation of Soups and Gravies 0.1-5.0 parts by weight of the mixed extract of the present invention were added to soups and gravies to prepare processed meat products for health promotion, soups and gravies for noodles.

<2-3> Preparation of Ground Beef 10 parts by weight of the mixed extract of the present invention were added to ground beef to prepare ground beef for health promotion.

<2-4> Preparation of Dairy Products

Various dairy products such as butter and ice cream were prepared by adding 5-10 parts by weight of the mixed extract of the present invention to milk and using the mixture.

<2-5> Preparation of Sunsik (Grain Powder)

Brown rice, barley, glutinous rice and coix (job's tear) were gelatinized by a conventional method, followed by drying. The dried mixture was distributed and pulverized, resulting in 60-mesh size grain powders.

Black bean, black sesame and perilla were steamed and dried by a conventional method. The dried mixture was distributed and pulverized, resulting in 60-mesh size grain powders.

The mixed extract of the present invention was vacuum-concentrated under reduced pressure using a vacuum concentrator, which was then spray-dried with a hot-air drier. The dried material was pulverized by a grinder, resulting in 60-mesh size grain powders.

The prepared grain, seeds, and the mixed extract of the present invention were mixed at the following ratio.

Grain (brown rice 30 parts by weight, coix 15 parts by weight, barley 20 parts by weight),
Seeds (perilla 7 parts by weight, black bean 8 parts by weight, black sesame 7 parts by weight),
The mixed extract of the present invention (3 parts by weight),
*Ganoderma lucidum* (0.5 parts by weight),
*Rehmannia glutinosa* (0.5 parts by weight).

Preparation Example 3

Preparation of Beverages

<3-1> Preparation of Health Beverages

Minor ingredients such as high fructose corn syrup (0.5%), oligosaccharide (2%), sugar (2%), salt (0.5%) and water (75%) were mixed homogeneously with 5 g of the mixed extract of the present invention, followed by flash pasteurization. The mixture was put in a small container such as a glass bottle or PET bottle, resulting in health beverages.

<3-2> Preparation of Vegetable Juice 5 g of the mixed extract of the present invention was added to 1,000 mL of tomato or carrot juice to prepare vegetable juice.

<3-3> Preparation of Fruit Juice 1 g of the mixed extract of the present invention was added to 1,000 mL of apple or grape juice to prepare fruit juice.

---

What is claimed is:

1. A method for treating inflammation, arthritis, or disc diseases in an individual in need thereof, comprising administering to said individual a pharmaceutically effective amount of an extract of Cibotii Rhizoma, Ledebouriellae Radix, Achyranthis Radix, *Paeonia lactiflora* Pall, and Glycyrrhizae Radix at a ratio 1 to 2:1 to 2:1 to 2:1 to 2:1 to 2, respectively.

2. The method as set forth in claim 1, wherein the extract is extracted with a solvent selected from water, ethanol, methanol or a mixture thereof.

3. The method as set forth in claim 1, wherein the extract inhibits NO production.

4. The method as set forth in claim 1, wherein the extract inhibits expressions of cyclooxygenase-2 (COX-2) and MMPs.

5. The method as set forth in claim 1, wherein the extract inhibits pains.

6. The method as set forth in claim 1, wherein the extract inhibits edema.

7. The method as set forth in claim 1, wherein the extract has nerve cell regenerative and nerve cell protective effects.

8. The method as set forth in claim 1, wherein the arthritis is any one selected from the group consisting of osteoarthritis, Rheumatoid arthritis, ankylosing spondylitis, reactive arthritis, psoriatic arthritis, Systemic lupus erythematosus, polymyositis, and polymyalgia rhematica.

9. A treatment method of inhibiting arthritis edema in an individual in need thereof, comprising administering to said individual a pharmaceutically effective amount of an extract of Cibotii Rhizoma, Ledebouriellae Radix, Achyranthis Radix, *Paeonia lactiflora* Pall, and Glycyrrhizae Radix at a ratio 1 to 2:1 to 2:1 to 2:1 to 2:1 to 2, respectively.

10. The treatment method as set forth in claim 9, wherein the arthritis is any one selected from the group consisting of osteoarthritis, Rheumatoid arthritis, ankylosing spondylitis, reactive arthritis, psoriatic arthritis, Systemic lupus erythematosus, polymyositis, and polymyalgia rhematica.

11. A method for treating a disc disease in an individual in need thereof, comprising administering to said individual a pharmaceutically effective amount of an extract of Cibotii Rhizoma, Ledebouriellae Radix, Achyranthis Radix, *Paeonia lactiflora* Pall, and Glycyrrhizae Radix at a ratio 1 to 2:1 to 2:1 to 2:1 to 2:1 to 2, respectively.

12. A method of inhibiting inflammatory pain in an individual in need thereof, comprising administering to said individual a pharmaceutically effective amount of an extract of Cibotii Rhizoma, Ledebouriellae Radix, Achyranthis Radix, *Paeonia lactiflora* Pall, and Glycyrrhizae Radix at a ratio 1 to 2:1 to 2:1 to 2:1 to 2:1 to 2, respectively.

* * * * *

SEQUENCE LISTING

<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: cox 2 for forward primer

<400> SEQUENCE: 1
gctggcctgg tactcagtag gtt     23

```
<210> SEQ ID NO 2
<211> LENGTH: 22
<212> TYPE: DNA
<213> ORGANISM: Artificial Sequence
<220> FEATURE:
<223> OTHER INFORMATION: cox 2 for reverse primer

<400> SEQUENCE: 2
cgaggccact gatacctatt gc                                              22

<210> SEQ ID NO 3
<211> LENGTH: 20
<212> TYPE: DNA
<213> ORGANISM: Artificial Sequence
<220> FEATURE:
<223> OTHER INFORMATION: iNOS for forward primer

<400> SEQUENCE: 3
cctggaggtt ctggatgaga                                                 20

<210> SEQ ID NO 4
<211> LENGTH: 20
<212> TYPE: DNA
<213> ORGANISM: Artificial Sequence
<220> FEATURE:
<223> OTHER INFORMATION: iNOS for reverse primer

<400> SEQUENCE: 4
gtagtagcgg ggcttcaaga                                                 20

<210> SEQ ID NO 5
<211> LENGTH: 24
<212> TYPE: DNA
<213> ORGANISM: Artificial Sequence
<220> FEATURE:
<223> OTHER INFORMATION: MMP 13 for forward primer

<400> SEQUENCE: 5
acgttcaagg aatccagtct ctct                                            24

<210> SEQ ID NO 6
<211> LENGTH: 21
<212> TYPE: DNA
<213> ORGANISM: Artificial Sequence
<220> FEATURE:
<223> OTHER INFORMATION: MMP 13 for reverse primer

<400> SEQUENCE: 6
ggatagggct gggtcacact t                                               21

<210> SEQ ID NO 7
<211> LENGTH: 22
<212> TYPE: DNA
<213> ORGANISM: Artificial Sequence
<220> FEATURE:
<223> OTHER INFORMATION: GAPDH for forward primer

<400> SEQUENCE: 7
tggcctccaa ggagtaagaa ac                                              22

<210> SEQ ID NO 8
<211> LENGTH: 20
<212> TYPE: DNA
<213> ORGANISM: Artificial Sequence
```

```
<220> FEATURE:
<223> OTHER INFORMATION: GAPDH for reverse primer

<400> SEQUENCE: 8
cagcaactga gggcctctct                                                    20
```